US008047206B2

(12) United States Patent
Boucher et al.

(10) Patent No.: US 8,047,206 B2
(45) Date of Patent: Nov. 1, 2011

(54) MAGNETIC DEVICES, SYSTEMS, AND METHODS PLACED IN OR ON A TONGUE

(75) Inventors: Ryan P. Boucher, San Francisco, CA (US); Joe Paraschac, San Jose, CA (US); Edward M. Gillis, San Jose, CA (US); Eric N. Doelling, Sunnyvale, CA (US); Craig A. Purdy, Sunnyvale, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1149 days.

(21) Appl. No.: 11/404,631

(22) Filed: Apr. 14, 2006

(65) Prior Publication Data

US 2006/0289015 A1 Dec. 28, 2006

Related U.S. Application Data

(63) Continuation-in-part of application No. 11/397,361, filed on Apr. 4, 2006, now abandoned, which is a continuation-in-part of application No. 10/806,372, filed on Mar. 22, 2004, now Pat. No. 7,441,559, which is a continuation-in-part of application No. 10/718,254, filed on Nov. 20, 2003, now Pat. No. 7,360,542, which is a continuation-in-part of application No. 10/656,861, filed on Sep. 6, 2003, now Pat. No. 7,188,627, which is a continuation-in-part of application No. 10/236,455, filed on Sep. 6, 2002, now Pat. No. 7,216,648.

(60) Provisional application No. 60/441,639, filed on Jan. 22, 2003, provisional application No. 60/456,164, filed on Mar. 20, 2003, provisional application No. 60/739,519, filed on Nov. 23, 2005, provisional application No. 60/754,939, filed on Dec. 29, 2005.

(51) Int. Cl.
*A61F 13/00* (2006.01)

(52) U.S. Cl. ........................................ 128/848; 602/902

(58) Field of Classification Search ................. 128/848, 128/859–862; 600/12; 623/18.12; 602/902; 433/6

See application file for complete search history.

(56) References Cited

U.S. PATENT DOCUMENTS

| 4,304,227 A | 12/1981 | Samelson |
| 4,850,963 A * | 7/1989 | Sparks et al. ............ 600/29 |
| 4,978,323 A | 12/1990 | Freedman |
| 5,019,372 A | 5/1991 | Folkman et al. |
| 5,176,618 A | 1/1993 | Freedman |
| 5,220,918 A | 6/1993 | Heide et al. |
| 5,373,859 A | 12/1994 | Forney |
| 5,465,734 A | 11/1995 | Alvarez et al. |
| 5,649,540 A | 7/1997 | Alvarez et al. |
| 5,792,067 A | 8/1998 | Karell |

(Continued)

FOREIGN PATENT DOCUMENTS

DE 4307262 3/1993

*Primary Examiner* — Michael A. Brown

(57) ABSTRACT

Magnetic structures develop a magnetic force between a tongue and a posterior pharyngeal wall to stabilize an orientation of the tongue. The magnetic structures include magnetic materials that are sized, configured, and arranged on at least one of the first and second magnetic structures, to maintain a substantially mutually repelling orientation between the first and second magnetic structures during a native range of movement of the tongue relative to the pharyngeal wall, i.e., during swallowing and/or drinking/and or speech.

14 Claims, 31 Drawing Sheets

U.S. PATENT DOCUMENTS

| | | | |
|---|---|---|---|
| 5,817,000 A * | 10/1998 | Souder | 600/15 |
| RE36,120 E | 3/1999 | Karell | |
| 5,979,456 A | 11/1999 | Magovern | |
| 5,988,171 A | 11/1999 | Sohn et al. | |
| 6,231,496 B1 | 5/2001 | Wilk et al. | |
| 6,244,865 B1 | 6/2001 | Nelson et al. | |
| 6,250,307 B1 | 6/2001 | Conrad et al. | |
| 6,387,096 B1 * | 5/2002 | Hyde, Jr. | 606/60 |
| 6,390,096 B1 | 5/2002 | Conrad et al. | |
| 6,401,717 B1 | 6/2002 | Conrad et al. | |
| 6,408,851 B1 | 6/2002 | Karell | |
| 6,415,796 B1 | 7/2002 | Conrad et al. | |
| 6,450,169 B1 | 9/2002 | Conrad et al. | |
| 6,490,885 B1 | 12/2002 | Wilkinson | |
| 6,523,541 B2 | 2/2003 | Knudson et al. | |
| 6,523,542 B2 | 2/2003 | Knudson et al. | |
| 6,636,767 B1 | 10/2003 | Knudson et al. | |
| 6,742,524 B2 | 6/2004 | Knudson et al. | |
| 6,955,172 B2 | 10/2005 | Nelson et al. | |
| 7,073,505 B2 | 7/2006 | Nelson et al. | |
| 7,077,143 B2 | 7/2006 | Knudson et al. | |
| 7,077,144 B2 | 7/2006 | Knudson et al. | |
| 7,188,627 B2 | 3/2007 | Nelson et al. | |
| 2001/0047805 A1 | 12/2001 | Scarberry et al. | |
| 2002/0066702 A1 | 6/2002 | Liu | |
| 2004/0112390 A1 | 6/2004 | Brooks et al. | |
| 2005/0092332 A1 | 5/2005 | Conrad et al. | |

* cited by examiner

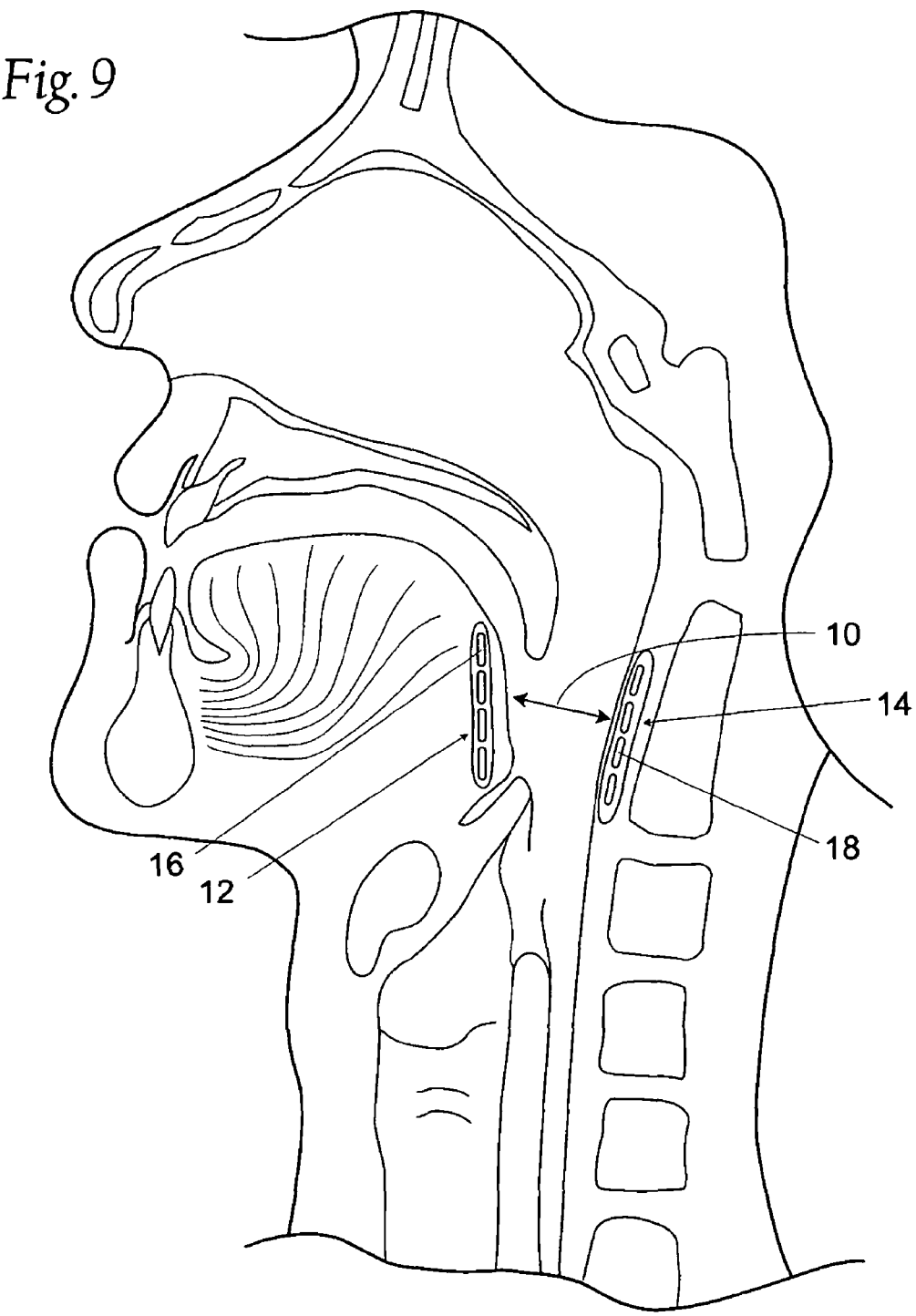

Upward Movement of Tongue

Magnetic implant will try to re-orient to attracting mode tendency to "flip"

The Edge Effect

Downward Movement of Tongue

Magnetic implant will try to re-orient to attracting mode tendency to "flip"

Angling the field of the magnet

Wedge Magnent

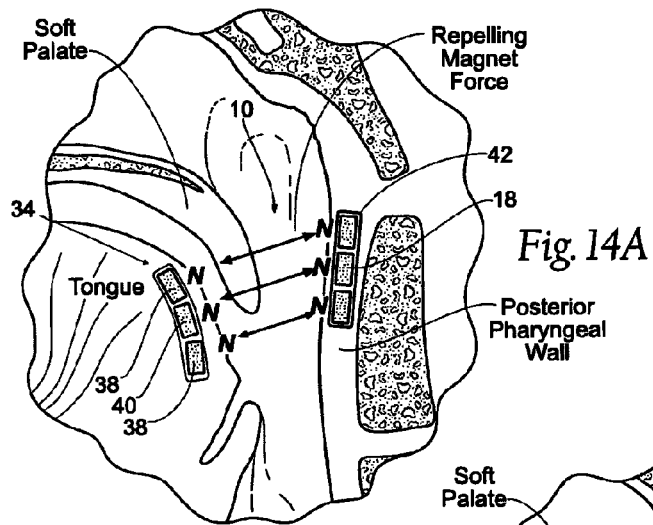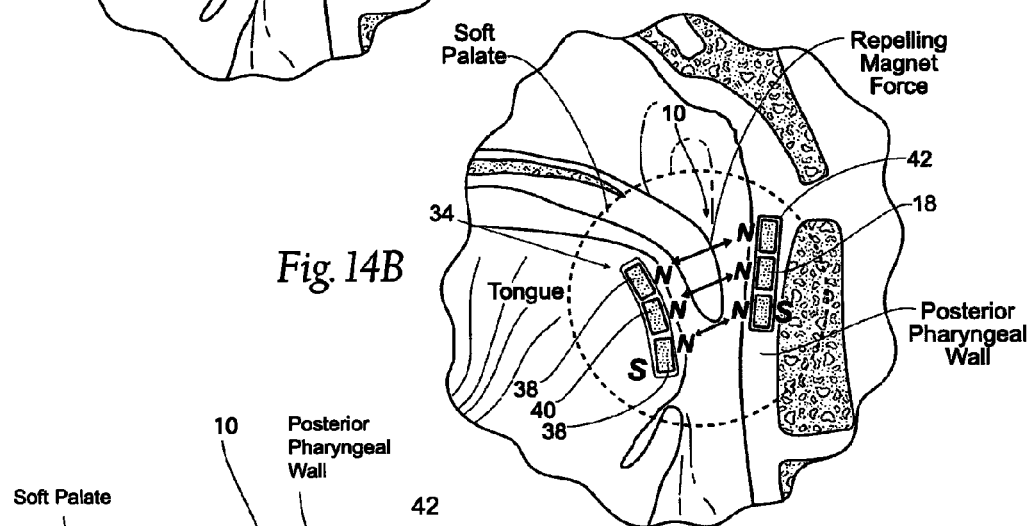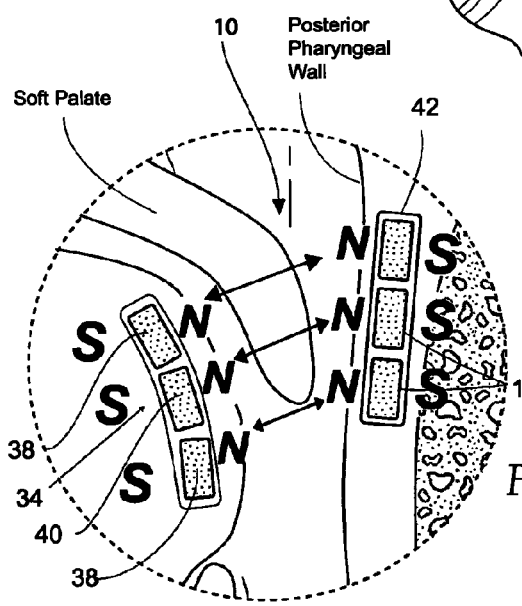

Fig. 15A
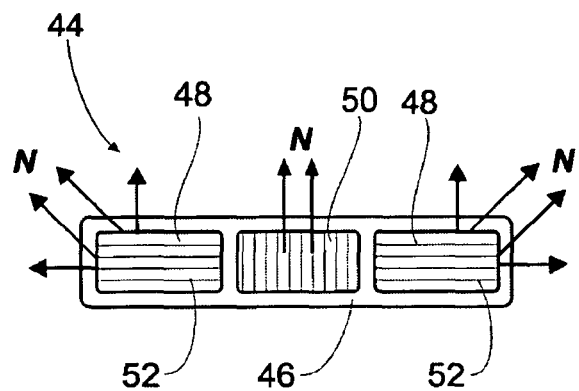
Fig. 15B
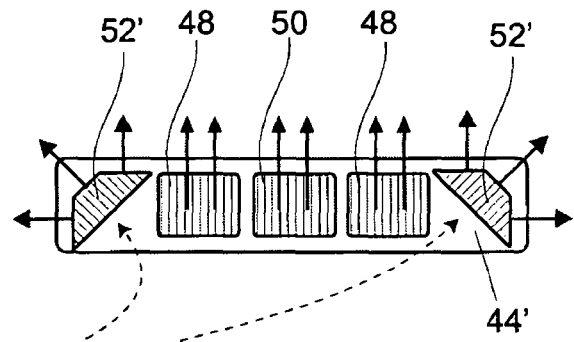
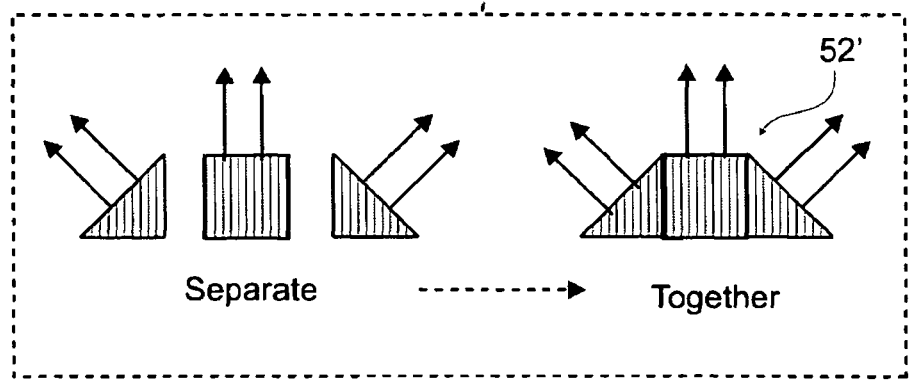
Separate ----→ Together

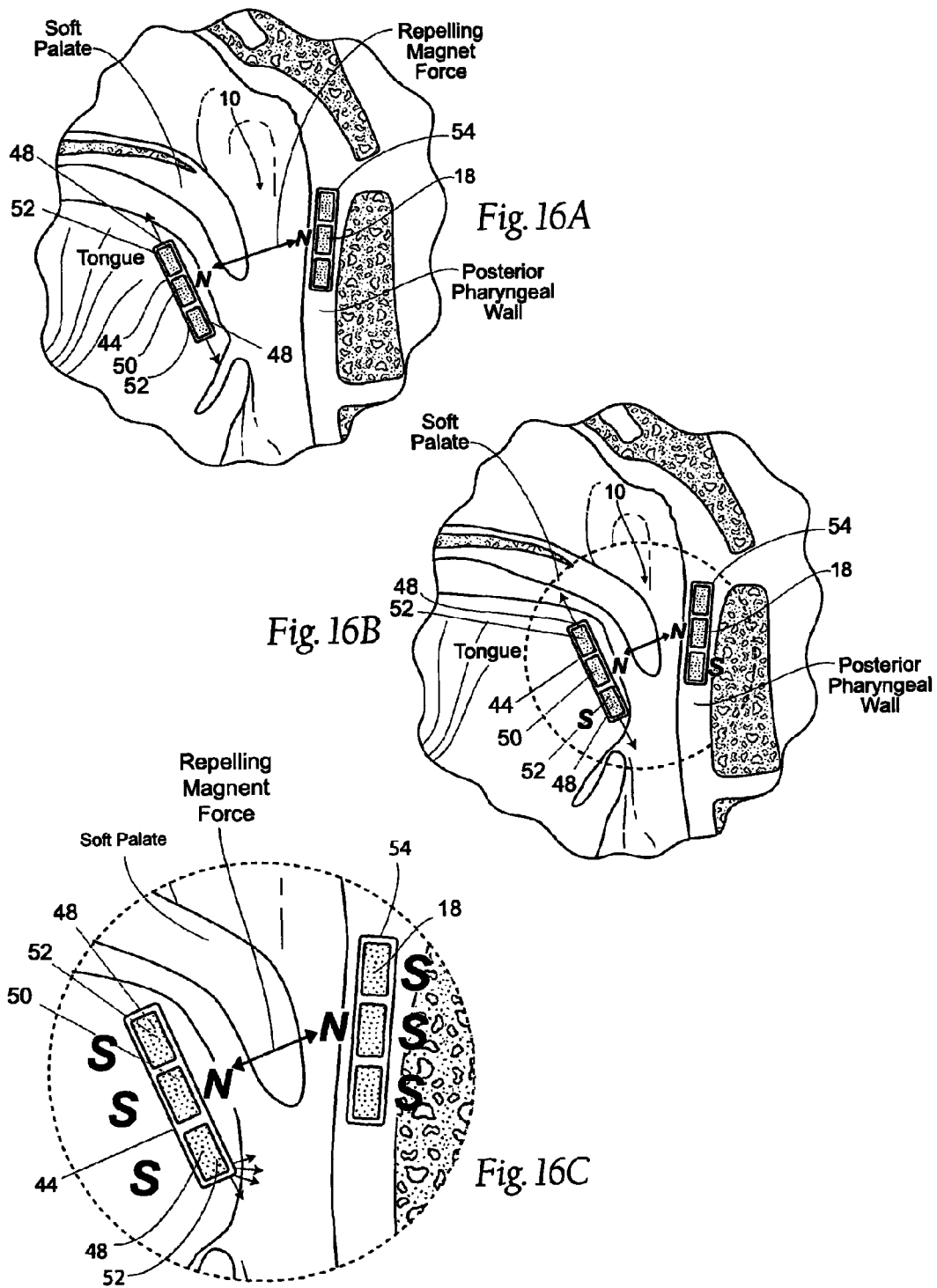

Magnetic implants
in a stable position

Magnetic implants
in a stable position

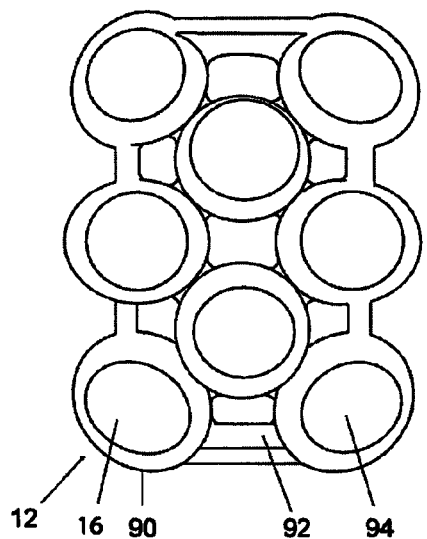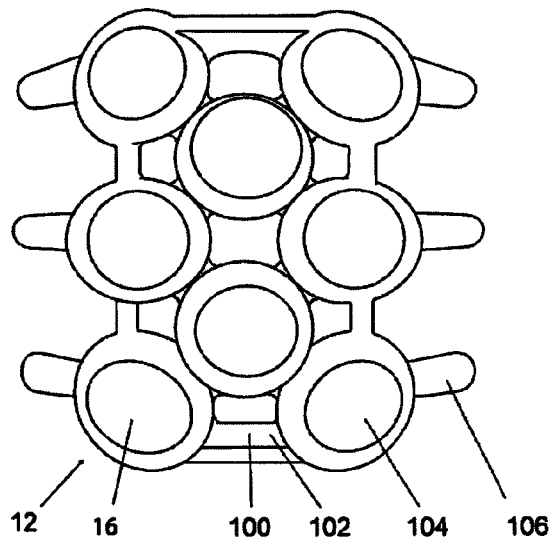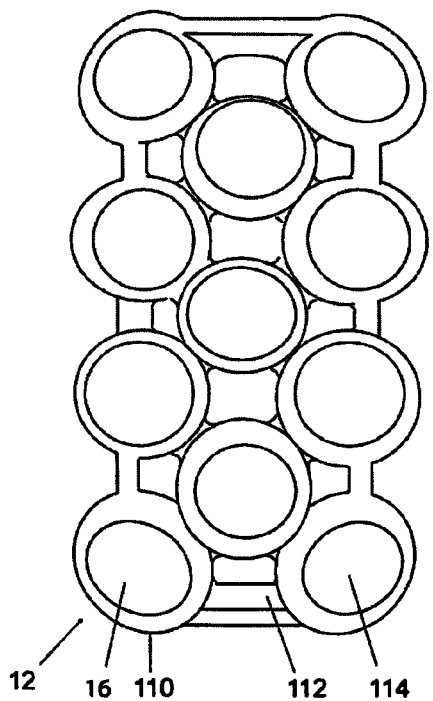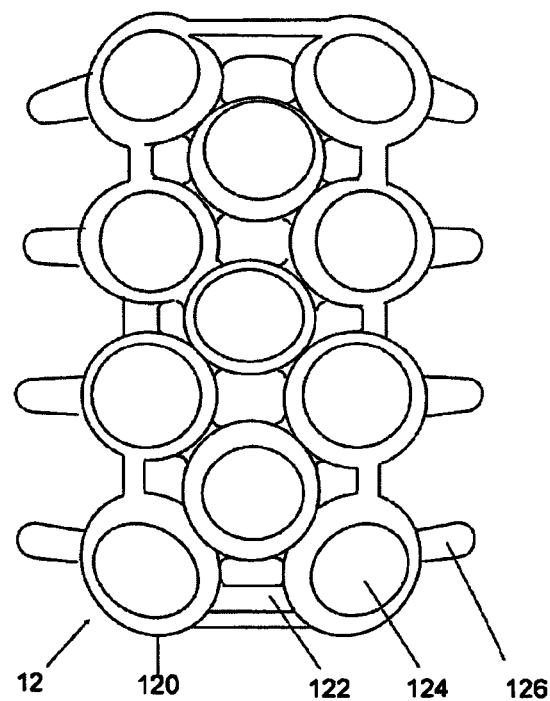

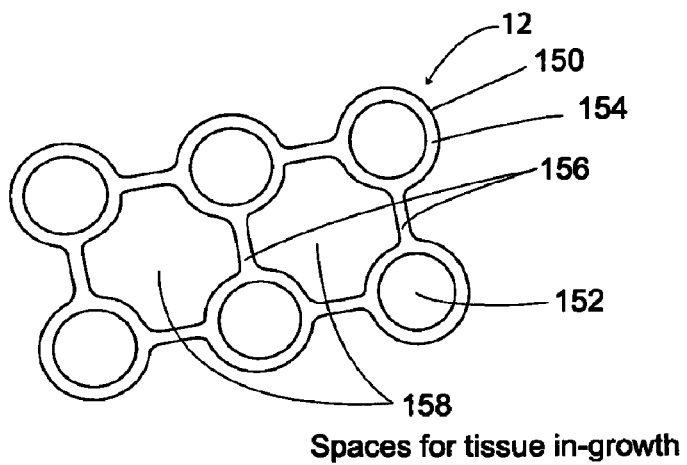
Fig. 27D — Spaces for tissue in-growth
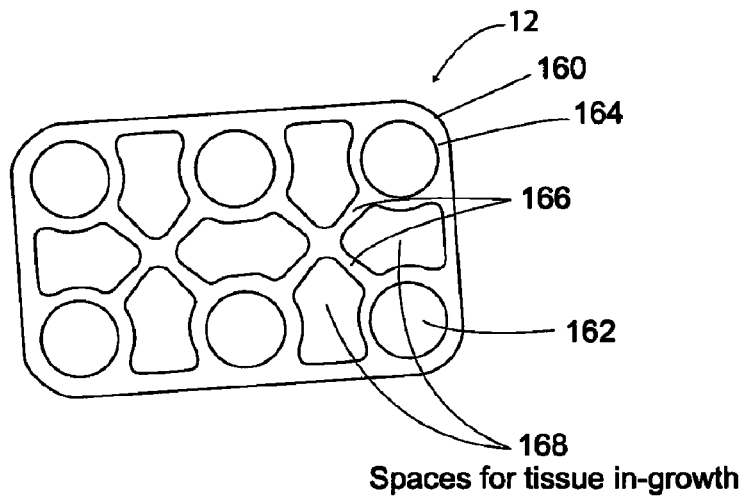
Fig. 27E — Spaces for tissue in-growth
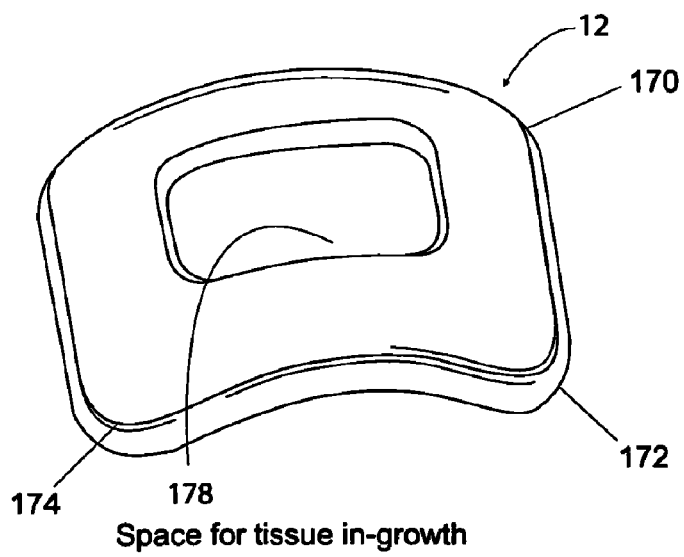
Fig. 27F — Space for tissue in-growth

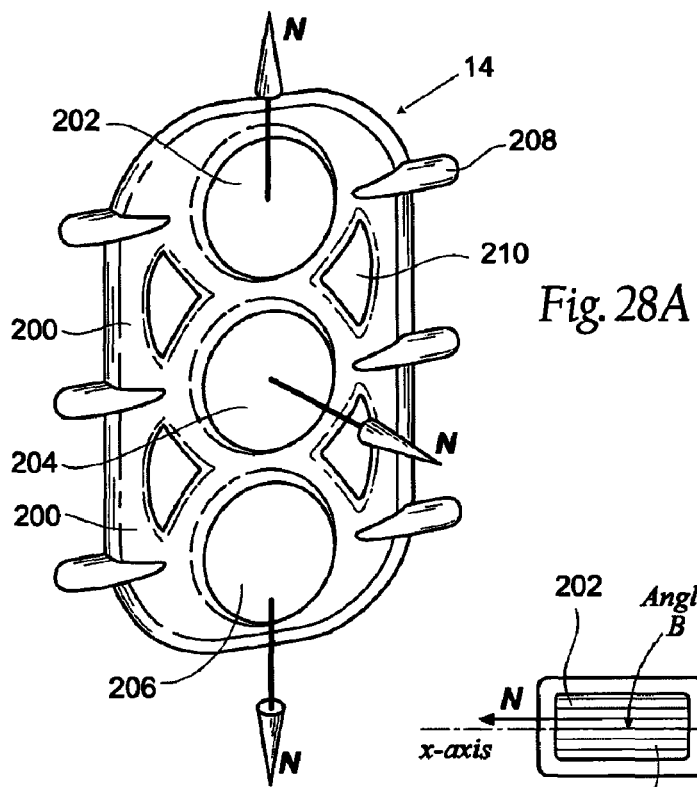
*Fig. 28A*
*Fig. 28B*
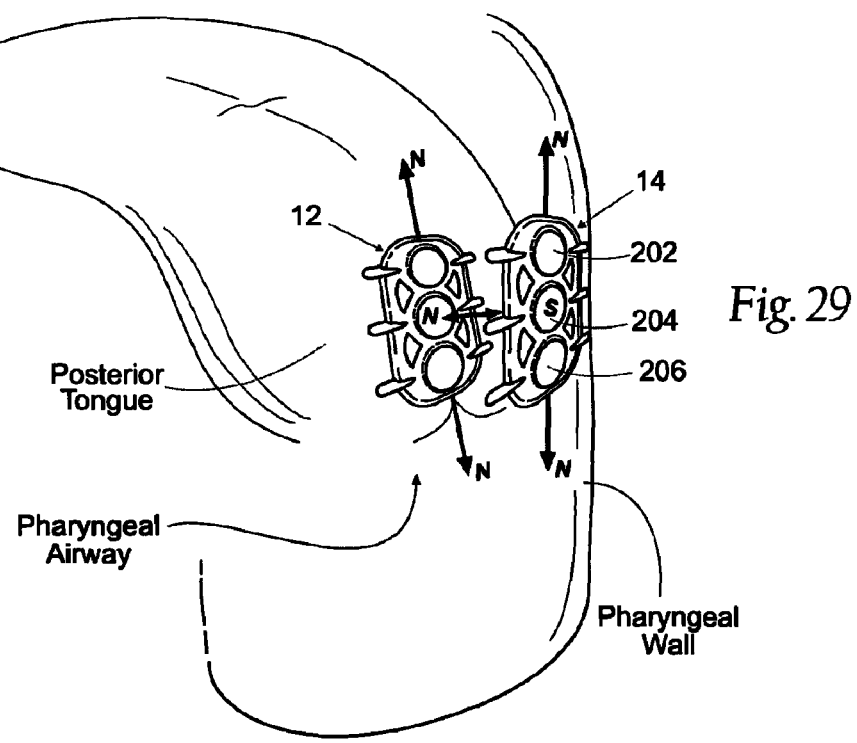
*Fig. 29*

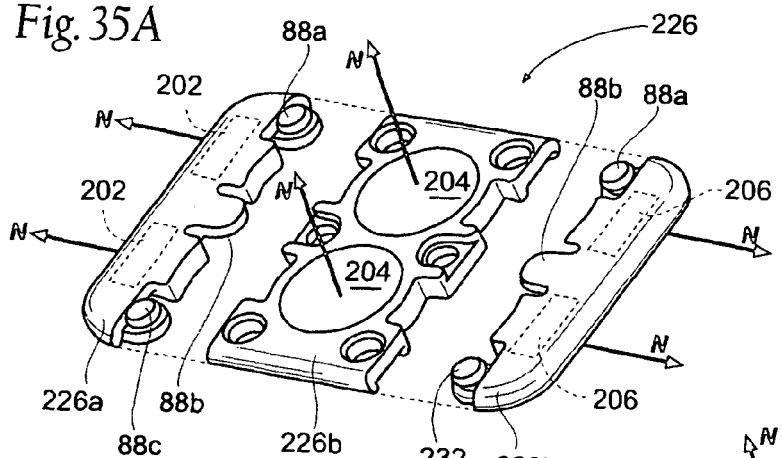
Fig. 35A
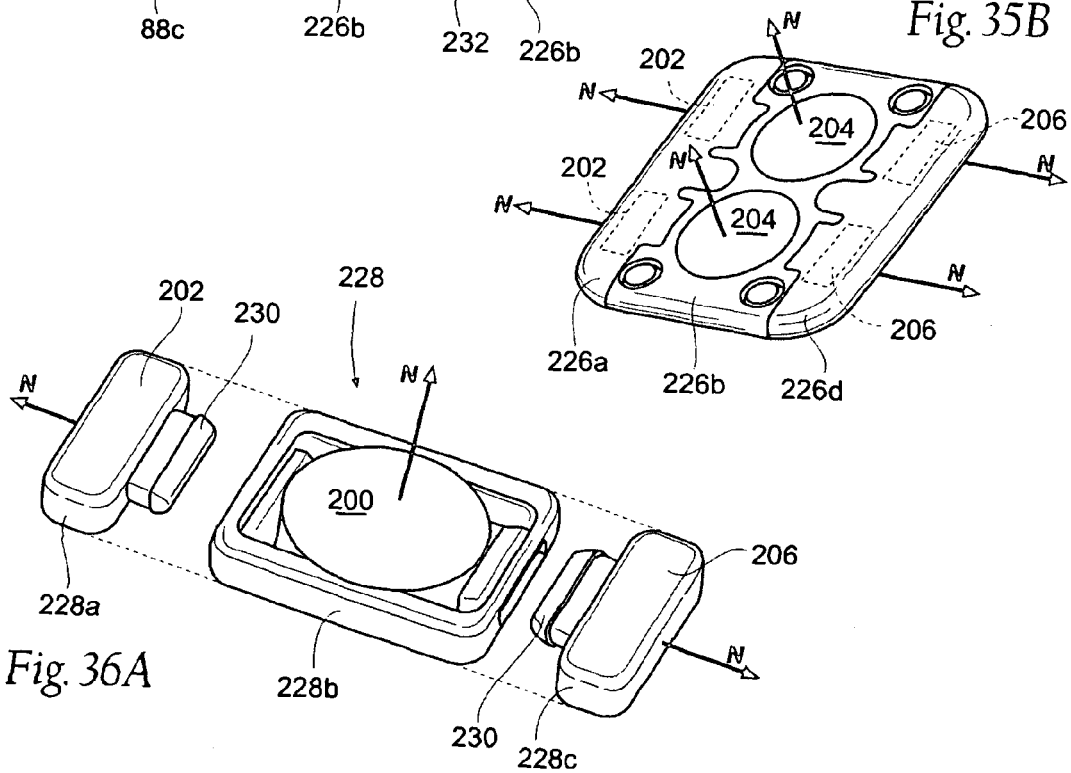
Fig. 35B
Fig. 36A
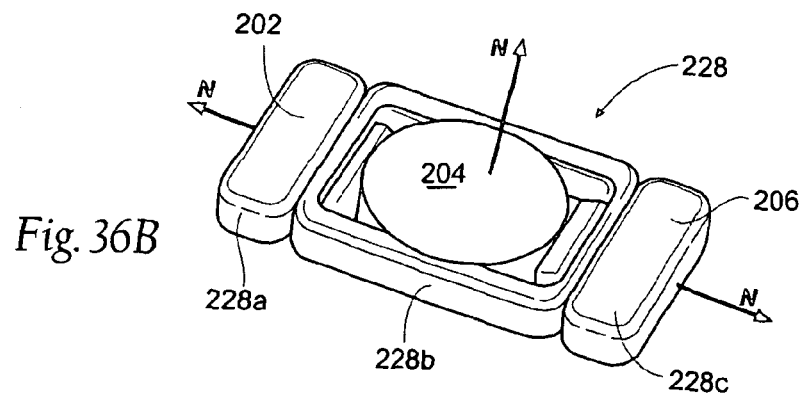
Fig. 36B

MAGNETIC DEVICES, SYSTEMS, AND METHODS PLACED IN OR ON A TONGUE

RELATED APPLICATIONS

This application is a continuation-in-part of U.S. patent application Ser. No. 11/397,361, filed Apr. 4, 2006 now abandoned entitled "Devices, Systems, and Methods Using Magnetic Force Systems In or On Soft Palate Tissue," which is a continuation-in-part of U.S. patent application Ser. No. 10/806,372, filed Mar. 22, 2004 now U.S. Pat. No. 7,441,559 entitled "Devices, Systems, and Methods to Fixate Tissue Within the Regions of the Body, Such as the Pharyngeal Conduit," which is a continuation-in-part of U.S. patent application Ser. No. 10/718,254, filed Nov. 20, 2003 now U.S. Pat. 7,360,542 entitled "Devices, Systems, and Methods to Fixate Tissue Within the Regions of the Body, Such as the Pharyngeal Conduit," which is a continuation-in-part of U.S. patent application Ser. No. 10/656,861, filed Sep. 6, 2003 now U.S. Pat. No. 7,188,627 entitled "Magnetic Force Devices, Systems, and Methods for Resisting Tissue Collapse within the Pharyngeal Conduit," which further claims the benefit of U.S. Provisional Patent Application Ser. No. 60/441,639, filed Jan. 22, 2003 and U.S. Provisional Patent Application Ser. No. 60/456,164, filed Mar. 20, 2003, and which is a continuation-in-part of U.S. patent application Ser. No. 10/236,455, filed Sep. 6, 2002 now U.S. Pat .No. 7,216,648 and entitled "System and Method for Moving and/or Restraining Tissue in the Upper Respiratory System." This application also claims the benefit of U.S. Provisional Patent Application Ser. No. 60/739,519, filed Nov. 23, 2005 and U.S. Provisional Patent Application Ser. No. 60/754,839, filed Dec. 29, 2005.

FIELD OF THE INVENTION

The invention is directed to devices, systems, and methods for the treatment of sleep disordered breathing including snoring and obstructive sleep apnea.

BACKGROUND OF THE INVENTION

I. Characteristics of Sleep Apnea

First described in 1965. sleep apnea is a breathing disorder characterized by brief interruptions (10 seconds or more) of breathing during sleep. Sleep apnea is a common but serious, potentially life-threatening condition, affecting as many as 18 million Americans. Snoring can also occur independent of or during a sleep apneic event.

There are two types of sleep apnea: central and obstructive. Central sleep apnea, occurs when the brain fails to send the appropriate signal to the breathing muscles to initiate respirations, e.g., as a result of brain stem injury or damage. Mechanical ventilation is the only treatment available to ensure continued breathing.

Obstructive sleep apnea (OSA) is far more common. Normally, the muscles of the upper part of the throat keep the airway open to permit air flow into the lungs. When the muscles at the base of the tongue and the uvula (the small fleshy tissue hanging from the center of the back of the throat) relax and sag, the relaxed tissues may vibrate as air flows past the tissues during breathing, resulting in snoring. Snoring affects about half of men and 25 percent of women—most of whom are age 50 or older.

In more serious cases, the airway becomes blocked, making breathing labored and noisy, or even stopping it altogether. In a given night, the number of involuntary breathing pauses or "apneic events" may be as high as 20 to 30 or more per hour. These breathing pauses are almost always accompanied by snoring between apnea episodes, although not everyone who snores has the condition. Sleep apnea can also be characterized by choking sensations.

Lack of air intake into the lungs results in lower levels of oxygen and increased levels of carbon dioxide in the blood. The altered levels of oxygen and carbon dioxide alert the brain to resume breathing and cause arousal. The frequent interruptions of deep, restorative sleep often lead to early morning headaches, excessive daytime sleepiness, depression, irritability, and learning and memory difficulties.

The medical community has become aware of the increased incidence of heart attacks, hypertension and strokes in people with moderate or severe obstructive sleep apnea. It is estimated that up to 50 percent of sleep apnea patients have high blood pressure.

Upon an apneic event, the sleeping person is unable to continue normal respiratory function and the level of oxygen saturation in the blood is reduced. The brain will sense the condition and cause the sleeper to struggle and gasp for air. Breathing will then resume, often followed by continued apneic events. There are potentially damaging effects to the heart and blood vessels due to abrupt compensatory swings in blood pressure. Upon each event, the sleeping person will be partially aroused from sleep, resulting in a greatly reduced quality of sleep and associated daytime fatigue.

Although some apneic events are normal in all persons and mammals, the frequency of blockages will determine the seriousness of the disease and opportunity for health damage. When the incidence of blockage is frequent, corrective action should be taken.

II. The Anatomy of the Upper Airway

As FIG. 1 shows, the upper airway consists of a conduit that begins at the nasal valve, situated in the tip of the nose, and extends to the larynx, which is also called the voice box because it houses the vocal cords. The pharynx (which, in Greek, means "throat") is a cone-shaped passageway in the upper airway that leads from the oral and nasal cavities in the head to the esophagus and larynx. The pharynx serves both respiratory and digestive functions. Both circular and longitudinal muscles are present in the walls of this organ, which are called the pharyngeal walls. The circular muscles form constrictions that help push food to the esophagus and prevent air from being swallowed, while the longitudinal muscles lift the walls of the pharynx during swallowing.

The pharynx consists of three main divisions. The anterior portion is the nasal pharynx, the back section of the nasal cavity. The nasal pharynx connects to the second region, the oral pharynx, by means of a passage called an isthmus. The oral pharynx begins at the back of the mouth cavity and continues down the throat to the epiglottis, a flap of tissue that covers the air passage to the lungs and that channels food to the esophagus. The isthmus connecting the oral and nasal regions allows humans to breathe through either the nose or the mouth. The third region is the laryngeal pharynx, which begins at the epiglottis and leads down to the esophagus. Its function is to regulate the passage of air to the lungs and food to the esophagus. Air from the nasal cavity flows into the larynx, and food from the oral cavity is routed to the esophagus directly behind the larynx. The epiglottis, a cartilaginous, leaf-shaped flap, functions as a lid to the larynx and, during the act of swallowing, controls the traffic of air and food.

The mouth cavity marks the start of the digestive tube. Oval in shape, it consists of two parts: the vestibule and the mouth cavity proper.

The vestibule is the smaller outer portion, delimited externally by the lips and cheeks and internally by the gums and teeth. It connects with the body surface through the rima or orifice of the mouth. The vestibule receives the secretion of the parotid salivary glands and connects when the jaws are closed with the mouth cavity proper by an aperture on both sides behind the wisdom teeth, and by narrow clefts between opposing teeth.

The mouth cavity proper contains the tongue and is delimited laterally and in the front by the alveolar arches with the teeth therein contained. It receives the secretion from the submaxillary and sublingual salivary glands. The mouth cavity proper connects with the pharynx by a constricted aperture called isthmus faucium.

The tongue is a mobile muscular organ that can assume a variety of shapes and positions. The tongue has a relatively fixed inferior part that is attached to the hyoid bone and mandible. The rest of the tongue is called the body of the tongue. It is essentially a mass of muscles that is mostly covered by mucous membrane. The muscles in the tongue do not act in isolation. Some muscles perform multiple actions with parts of one muscle acting independently producing different, sometimes antagonistic, actions.

The tongue is partly in the mouth or oral cavity and partly in the pharynx. At rest, it occupies essentially all of the oral cavity. The posterior part of the tongue demarcates the posterior boundary of the oral cavity. Its mucous membrane is thick and freely movable.

The tongue is involved with mastication, taste, articulation, and oral cleansing. Its two main functions are forming words during speaking and squeezing food into the pharynx when swallowing.

The palate forms the arched roof of the oral or mouth cavity (the mouth) and the floor of the nasal cavities (the nose). It separates the oral cavity from the nasal cavities and the nasal pharynx. The palate consists of two regions—the hard palate anteriorly and the soft palate posteriorly.

The hard palate is vaulted and defines the space filled by the tongue when it is at rest. The hard palate has a hard bony skeleton, hence its name.

The soft palate has no bony skeleton, hence its name. The soft palate is suspended from the posterior border of the hard palate. It extends posteriorly and inferiorly as a curved free margin from which hangs a conical process, called the uvula. Muscles arise from the base of the cranium and descend into the soft palate. The muscles allow the soft palate to be elevated during swallowing into contact with the posterior pharyngeal wall. The muscles also allow the soft palate to be drawn inferiorly during swallowing into contact with the posterior part of the tongue.

The soft palate is thereby very dynamic and movable. When a person swallows, the soft palate initially is tensed to allow the tongue to press against it, to squeeze the bolus of food to the back of the mouth. The soft palate is then elevated posteriorly and superiorly against the pharyngeal wall, acting as a valve to prevent passage of food into the nasal cavity.

III. Sleep and the Anatomy of the Upper Airway

Although all tissue along this conduit is dynamic and responsive to the respiratory cycle, only the pharynx is totally collapsible. The pharyngeal structures and individual anatomic components within this region include the pharyngeal walls, the base of the tongue, the soft palate with uvula, and the epiglottis.

The cross sectional area of the upper airway varies with the phases of the respiratory cycle. At the initiation of inspiration (Phase I), the airway begins to dilate and then to remain relatively constant through the remainder of inspiration (Phase II). At the onset of expiration (Phase III) the airway begins to enlarge, reaching maximum diameter and then diminishing in size so that at the end of expiration (Phase IV), it is at its narrowest, corresponding to the time when the upper airway dilator muscles are least active, and positive intraluminal pressure is lowest. The upper airway, therefore, has the greatest potential for collapse and closure at end-expiration. [ref: Schwab R J, Goldberg A N. Upper airway assessment: radiographic and other imaging techniques. Otolaryngol Clin North Am 1998, 31:931-968]

Sleep is characterized by a reduction in upper airway dilator muscle activity. For the individual who snores or has obstructive sleep apnea (OSA) and perhaps the other disorders which comprise much of the group of entities called obstructive sleep-disordered breathing (SDB), it is believed that this change in muscle function causes pharyngeal narrowing and collapse. Two possible etiologies for this phenomenon in OSA patients have been theorized. One is that these individuals reduce the airway dilator muscle tone more than non-apneics during sleep (the neural theory). The other is that all individuals experience the same reduction in dilator activity in sleep, but that the apneic has a pharynx that is structurally less stable (the anatomic theory). Both theories may in fact be contributors to OSA, but current studies seem to support that OSA patients have an intrinsically structurally narrowed and more collapsible pharynx [ref: Isono S. Remmers J, Tanaka A Sho Y, Sato J, Nishino T. Anatomy of pharynx in patients with obstructive sleep apnea and in normal subjects. J Appl Physiol 1997:82:1319-1326.] Although this phenomenon is often accentuated at specific sites, such as the velopharyngeal level [Isono], studies of closing pressures [Isono] supports dynamic fast MRI imaging that shows narrowing and collapse usually occurs along the entire length of the pharynx. [ref: Shellock F G, Schatz C J, Julien P, Silverman J M, Steinberg F, Foo T K F, Hopp M L, Westbrook P R. Occlusion and narrowing of the pharyngeal airway in obstructive sleep apnea: evaluation by ultrafast spoiled GRASS M R imaging. Am J of Roentgenology 1992:158: 1019-1024.].

IV. Treatment Options

To date, the only modality that addresses collapse along the entire upper airway is mechanical positive pressure breathing devices, such as continuous positive airway pressure (CPAP) machines. All other modalities, such as various surgical procedures and oral appliances, by their nature, address specific sectors of the airway (such as palate, tongue base and hyoid levels), but leave portions of pharyngeal wall untreated. This may account for the considerably higher success rate of CPAP over surgery and appliances in controlling OSA. Although CPAP, which in essence acts as an airway splint for the respiratory cycle, is highly successful, it has some very significant shortcomings. It can be cumbersome to wear and travel with, difficult to accept on a social level, and not tolerated by many (for reasons such as claustrophobia, facial and nasal mask pressure sores, airway irritation). These factors have lead to a relatively poor long-term compliance rate. One study has shown that 65% of patients abandon their CPAP treatment in 6 months.

Other current treatments for OSA include genioglossal advancement (GA) and maxillomandibular advancement (MA). These treatments involve highly invasive surgical procedures and a long recovery time, and therefore have relatively low patient appeal.

The need remains for simple, cost-effective devices, systems, and methods for reducing or preventing sleep disordered breathing events.

SUMMARY OF THE INVENTION

The invention provides systems and methods that develop a magnetic force interacting with a tongue to maintain airway patency. The invention is particularly useful to prevent sleep disordered diseases such as snoring, obstructive sleep apnea (OSA) and hypopnea (a partial obstruction of the airway during sleep).

One aspect of the invention provides magnetic systems and methods comprising a first magnetic structure sized and configured for placement in or on a tongue, and a second magnetic structure sized and configure for placement in or on a pharyngeal wall. The first and second magnetic structures include magnetic materials that are sized, configured, and arranged on at least one of the first and second magnetic structures, to maintain a substantially mutually repelling orientation between the first and second magnetic structures during a native range of movement of the tongue relative to the pharyngeal wall, i.e., during swallowing and/or drinking/ and or speech.

Other aspects of the invention provide magnetic structures comprising a carrier sized and configured for placement in or on a tongue. A magnetic material is carried by the structure. According to these aspects of the invention, the size and configuration of the carrier can include one or more technical features or combinations of these technical features that magnetically and/or mechanically stabilize the structure on the tongue.

According to one aspect, the carrier can have a curved configuration corresponding to a natural shape of the tongue. In one arrangement, the curved configuration includes a first curved configuration along a first axis of the magnetic structure and a second curved configuration along a second axis of the magnetic structure.

According to another aspect, the carried can be capable of flexure in response to application of an external force. A magnetic material is carried by the structure. In one arrangement, the carrier can be capable of flexure in response to application of an external force more in one direction than in another direction.

According to another aspect, at least one radial magnetic is carried by the structure.

According to another aspect, first and second sources of magnetism can be carried on the carrier. Each source generates a magnetic field having a direction. The direction of the magnetic field of the first source of magnetism is oriented at an angle of from the direction of the magnetic field of the second source of magnetism.

Additional aspects of the invention provides systems and methods that orient the magnetic structure having one or more of the technical features described above with a second magnetic structure. The second magnetic structure is sized and configured to be placed in or on tissue in a desired orientation with the first magnetic structure to magnetically interact with the first magnetic structure.

In one arrangement, the second magnetic structure is placed in or on tissue in a posterior pharyngeal wall. On another arrangement, the second magnetic structure is placed on tissue outside an airway.

Other technical features shall be apparent based upon the accompanying description, drawings, and claims.

BRIEF DESCRIPTION OF THE DRAWINGS

FIG. 9 shows an anatomical sagittal cross-sectional view of human upper respiratory system with an illustrative repelling magnetic force system.

FIGS. 15A/B show embodiments of magnetic tongue implants with radial or variable magnetic field direction magnets.

FIGS. 28A/B show a frontal view and a longitudinal cross-section of an illustrative pharyngeal wall implant.

FIG. 29 shows an anatomical oblique and side-view of a tongue and a pharyngeal wall with illustrative implanted tongue and pharyngeal wall implants.

FIGS. 35A/B and 36A/B show alternative embodiments of three piece support carriers for pharyngeal wall implants.

DETAILED DESCRIPTION

This Specification discloses various magnetic implants and external devices, systems, and methods for the use of repelling magnetic force to maintain a patent airway. For example, the various aspects of the invention have application in procedures requiring the restriction of tissue collapse in and/or around the body, such as a passageway within the body. The devices, systems, and methods that embody features of the invention are also adaptable for use with devices, systems, and methods that are not restricted to tissue based applications.

The devices, systems, and methods are particularly well suited for treating sleep disordered breathing, including sleep apnea. For this reason, the devices, systems, and methods will be described in this context. Still, it should be appreciated that the disclosed devices, systems, and methods are applicable for use in treating other dysfunctions elsewhere in the body, which are not necessarily sleep disorder related.

I. The Tongue

A. Anatomy

Figure 1:
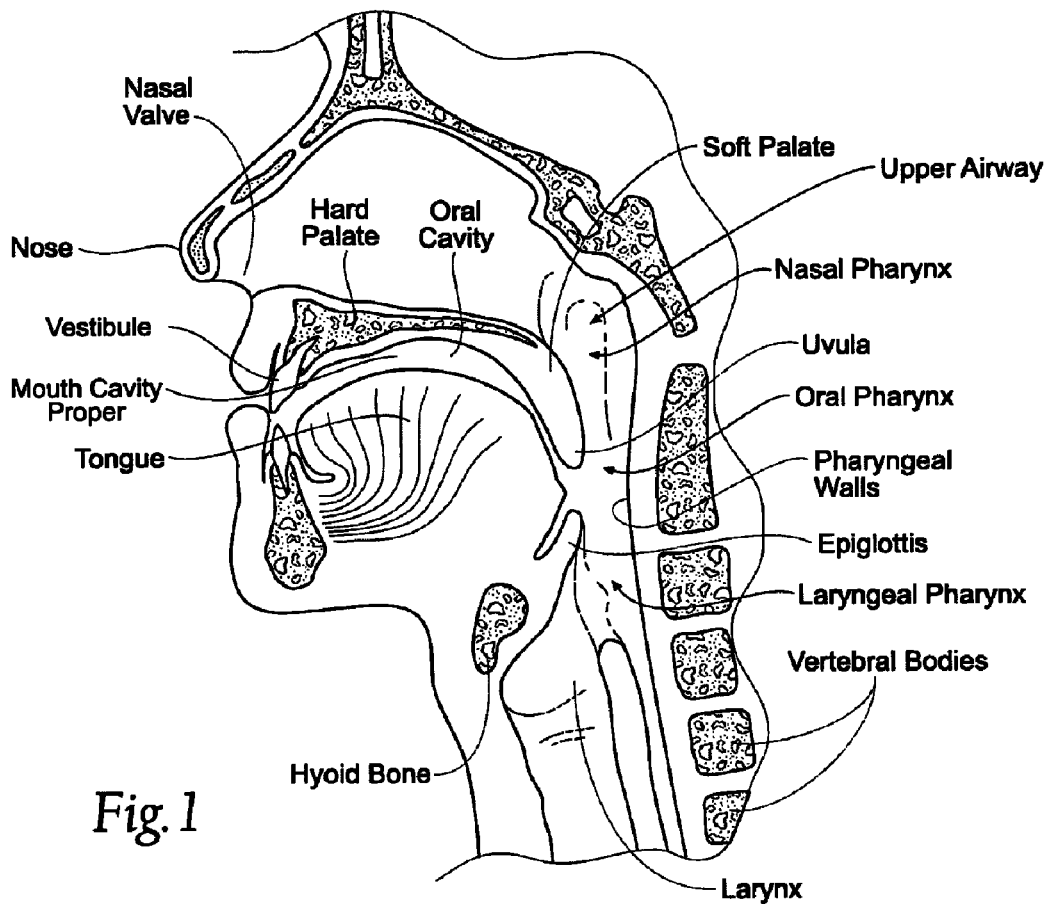
FIG. 1 is an anatomical sagittal cross-section of a normal human nasal airway, oral cavity, and oropharynx.
Figure 2:
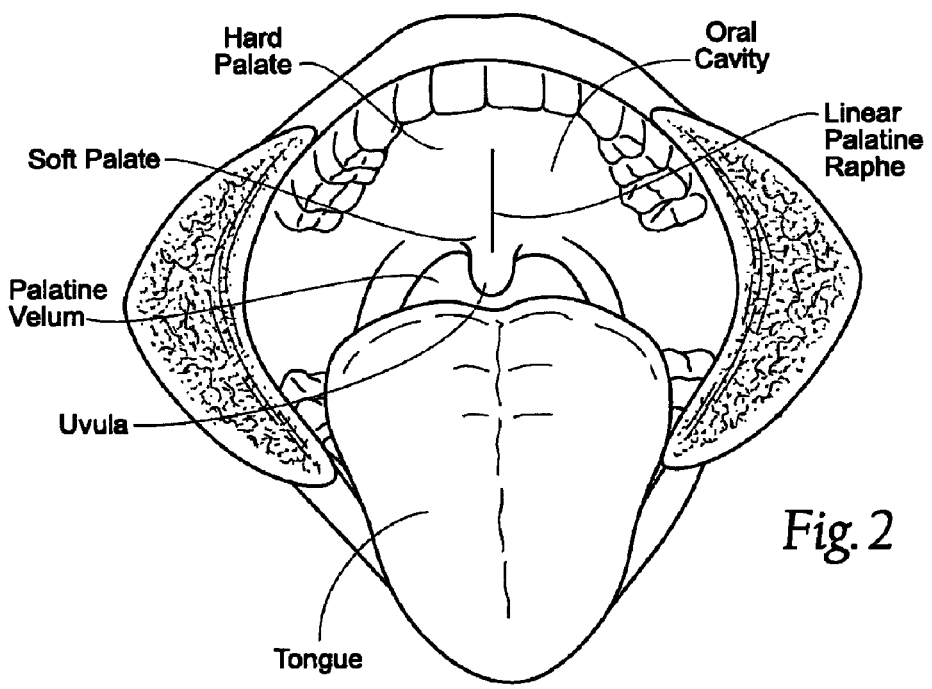
FIG. 2 is an anatomical view of the oral cavity.

FIG. 2 shows an anatomical view of the oral cavity, where the tongue has been pulled towards the front. FIG. 2 shows the tongue and the roof of the mouth, i.e., the palate, as previously described and as also shown in FIG. 1. FIG. 2 shows the two parts of the palate (which have also been previously described: namely, the hard palate (in the front) and the soft palate (in the back).

The tongue is located over the floor of the oral cavity. In human beings the tongue is an organ that undergoes a wide variety of movements, partly because it is involved in a broad range of activities, including speech, eating and swallowing. When a human is awake, the tongue normally moves in an up and forward position. When a human is asleep, the muscles of the tongue relax and the tongue is able to move in an even broader range of directions. This movement can occur laterally, posteriorly, anteriorly, cranially, caudally, in a rolling manner, or any combinations thereof.

The tongue can move in conjunction with other array structures (i.e. tongue and pharyngeal wall coming together or tongue and palate coming together) or independently of other structures, such as tongue movement without palate, posterior wall, or epiglottis movement.

B. The Tongue and Sleep Apnea

Sleep apnea occurs when the airway becomes obstructed; hypopnea occurs when the airway is partially obstructed. Sleep apnea takes many forms; closure of the airway can occur at any number of anatomical structures along the airway, including any combination of the tongue, soft palate, epiglottis, and pharyngeal wall. In particular, the tongue may collapse with respect to the pharyngeal wall, or both the base of the tongue and the pharyngeal wall may collapse at the same time. Thus, sleep apnea may be treated by preventing either the collapse of the tongue, or the collapse of the pharyngeal wall, or the collapse of both the tongue base and the pharyngeal wall.

Figure 3:
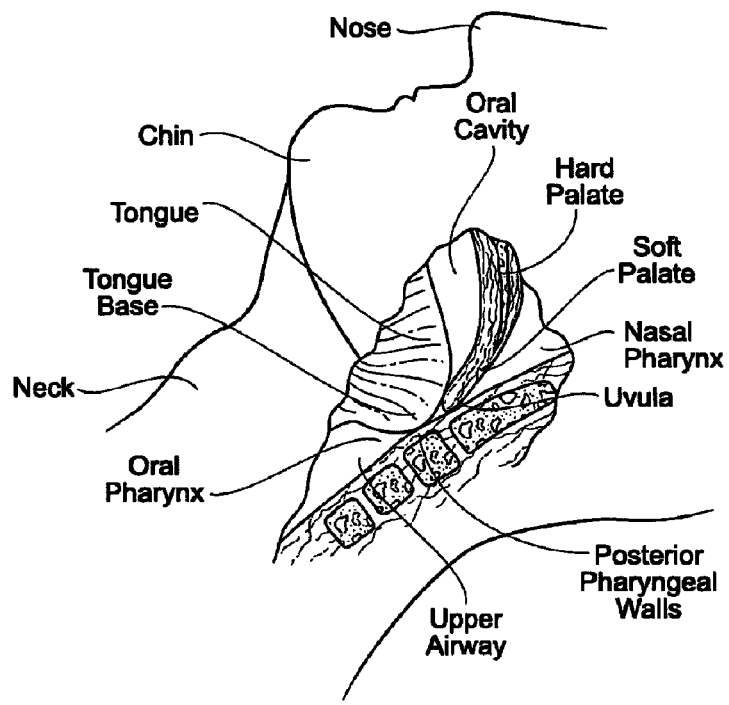
FIG. 3 is an anatomical side view of a patient with obstructive sleep apnea.

FIG. 1 is a sagittal cross section view of the upper airway system in a normal patient, showing the nasal and oral cavities, tongue, hard palate, soft palate, oropharynx, chin and neck. FIG. 3 shows a side view of a patient suffering from one form of sleep apnea involving the tongue. As shown in FIG. 3, the tongue base, the soft palate, and the uvula lean against the pharyngeal wall, effectively closing off the airway. An apneic attack can occur as a result.

II. Repelling Magnetic Force Systems

A. Overview

Figure 4:
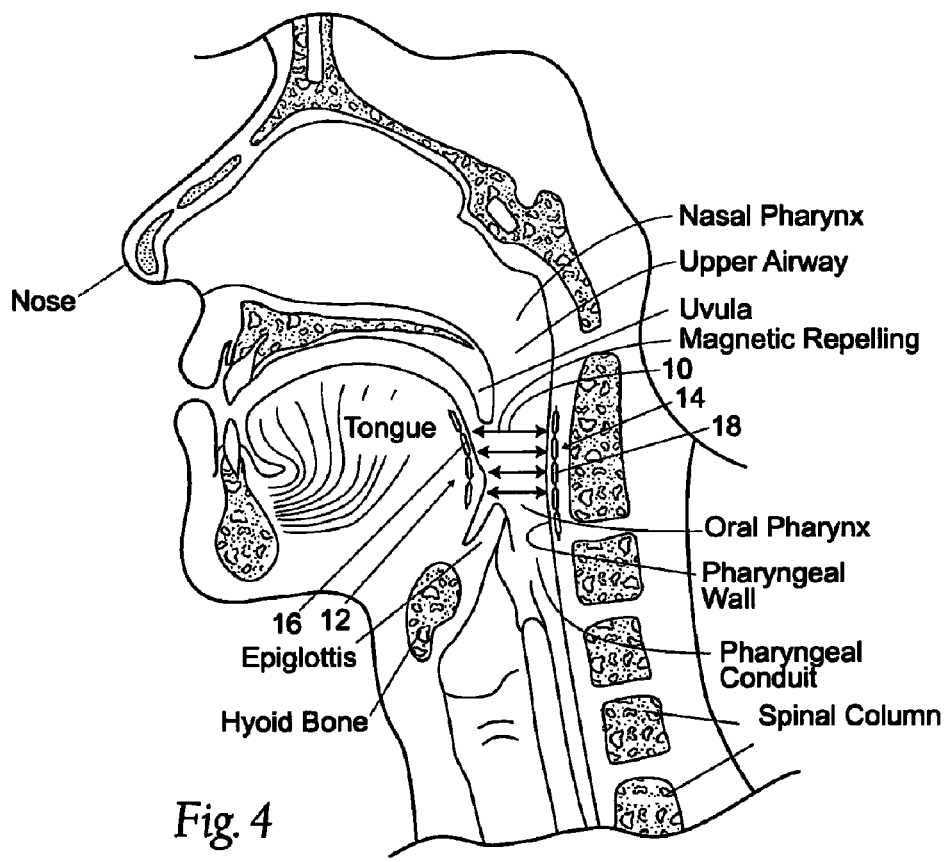
FIG. 4 is a view similar to FIG. 1, illustrating a magnetic repelling force system involving an internal magnetic tongue implant and an internal pharyngeal wall implant.

FIG. 4 shows in a diagrammatic way a magnetic force system 10 that resists occurrence of the tissue condition shown in FIG. 3, involving the collapse of the tongue against the pharyngeal wall. The magnetic force system 10 creates a magnetic force field in that location of the airway, which maintains the tongue in a position spaced away from the posterior pharyngeal wall, as FIG. 4 shows. The magnetic force field resists posterior movement of the tongue during sleep, keeping the airway open. An apneic episode is avoided.

The magnetic force system 10 can be variously constructed. In FIG. 4, the force system 10 includes two components 12 and 14. The first component 12 comprises one or more magnetic structures placed in or on tissue in the tongue. The second component 14 comprises one or more magnetic structures placed in or on the posterior pharyngeal wall generally aligned with the tongue. The magnetic structures or magnetic components 12 and 14 interact by developing a magnetic force between them, i.e., across the airway, which is indicated by arrows in FIG. 4.

The magnetic force can comprise a repelling force (i.e., a force in essentially an anterior-posterior direction between the tongue and posterior pharyngeal wall), and/or a torquing force (i.e., a force or moment of a force that tends to rotate the tongue about an axis), and/or a decentering force (i.e., a force in essentially a medial or side-to-side direction that tends to offset the tongue left or right), or a combination of two or more of these forces. The magnetic force between the two magnetic structures or magnetic components 12 and 14 resists the posterior movement of the tongue toward the posterior pharyngeal wall, or, stated differently, the magnetic force maintains separation between the tongue and the posterior pharyngeal wall, thereby preventing the occurrence of the airway-occluding tissue condition shown in FIG. 3. As FIG. 4 shows, the magnetic force between the first and second magnetic structures or magnetic components 12 and 14 keeps the airway open (i.e., patent) during sleep.

B. The Magnetic Structures

In its most basic form, the magnetic structures or magnetic components 12 and 14 of the magnetic force system 10 each comprise at least one magnetic material, respectively 16 and 18. The magnetic materials 16 and 18 are placed in or on the targeted tissue regions in a generally magnetically aligned relationship across the airway between the tongue and the pharyngeal wall. The magnetic materials 16 and 18 of the magnetic force system 10 are placed to magnetically interact and resist the collapse of tissue in the airway between the tongue and the pharyngeal wall during sleep.

1. Orientation of Like Poles

Each magnetic material 16 and 18 comprises a "hard" ferromagnetic material, which is also commonly referred to as a permanent magnet. A permanent magnet is characterized as a material showing resistance to external demagnetizing forces once being magnetized. That is, a high external magnetic field is required in order to remove the residual magnetism of a permanent magnet. Stated differently, a permanent magnet has very high intrinsic coercivity, which is a measure of its resistance to demagnetization.

A permanent magnet possesses poles of opposite polarity. The poles are regions of a magnet (usually at the end of the magnets) where the external magnetic field is strongest. Relative to Earth's magnetic poles, if the magnet is free to turn, one pole will point to the magnetic north pole of the Earth, and is thus called a north pole of the magnet, which is indicated by N in the drawings or otherwise called an N-pole. The opposite pole is called a south pole of the magnet, which is indicated by S in the drawings or otherwise called a S-pole.

According to physical laws, poles of like polarity (N-N or S-S) repel each other with a magnetic force. Conversely, poles of unlike polarity (N-S or S-N) attract each other with a magnetic force. Thus, structures incorporating permanent magnets will repel each other when like poles of the structures are oriented to face each other, and likewise attract each other when opposite poles of the structures are oriented to face each other. The magnitude of the force of magnetic attraction or repulsion depends on the strength of the magnets and the distance between the poles.

Examples of known permanent magnet materials include alloys of Neodymium-Iron-Boron (NdFeB), alloys of Aluminum-Nickel-Cobalt (AlNiCo), and Samarium Cobalt (SmCo). An electromagnet (current flowing through a coil of wire) can be substituted for a permanent magnet.

In the magnetic force system 10 shown in FIG. 4, the magnetic materials 16 and 18 are oriented such that like poles generally face each other across the airway (N-N or S-S). Thus, the first and second magnetic structures or magnetic components 12 and 14 are referred to as having the same polarity. The magnetic structures or magnetic components 12 and 14 will magnetically interact by the generation of a magnetic force between them. The nature of the magnetic force will generally be called in shorthand for purposes of description a "repelling" magnetic force, because of the interaction of magnetic poles of the same polarity. However, it should be appreciated that the magnetic force can include a torquing force (i.e., a force or moment of a force that tends to rotate the tongue about an axis), and/or a decentering force (i.e., a force in essentially a medial or side-to-side direction that tends to offset the tongue left or right), or a combination of two or more repelling, torquing, and decentralizing forces. One or more of these magnetic forces collectively prevent the tongue from moving in a posterior direction and closing or restricting the pharyngeal conduit or airway.

2. Configuration of the Magnetic Structures

Figure 5:
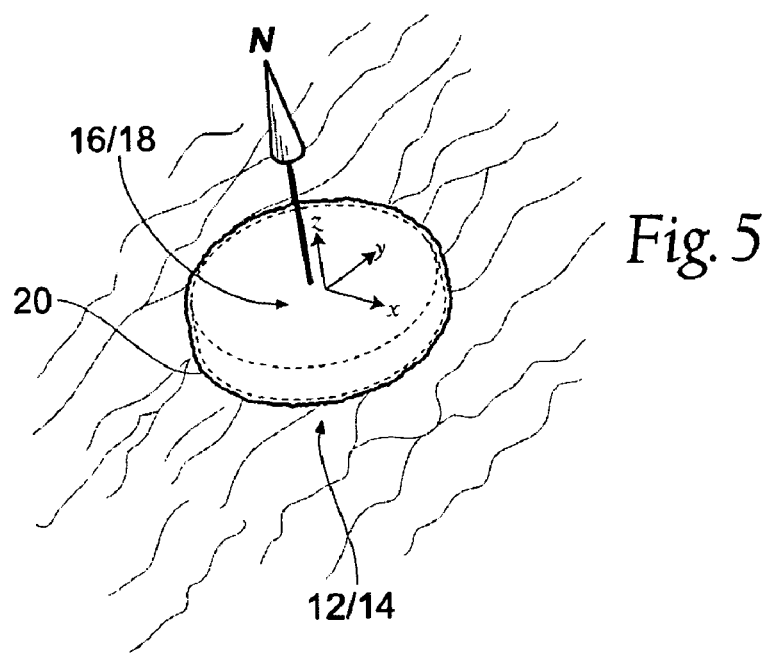
FIG. 5 shows an illustrative magnetic material.

As shown in FIG. 5, the magnetic materials 16 and 18 are placed in or on tissue. The term placed "in or on" is intended to mean that the magnetic materials 16 and 18 can be placed either on surface tissue or implanted within tissue. For longevity and comfort, the materials 16 and 18 are desirably implanted within tissue. In the illustrated embodiment, the magnetic material 16 is implanted within a region of the tongue. The magnetic material 18 is implanted in a posterior region of the pharyngeal wall.

The implanted permanent magnetic materials 16 and 18 can each be configured in various ways and take various shapes, e.g., cylindrical, square, rectangular, or other polygons. A given magnetic material 16 or 18 of a given magnetic structure or magnetic component 12 or 14 can comprise a single or discrete source of magnetism having a given desired polar orientation. For example, a given magnetic material 16 or 18 can comprise a single permanent magnet, as shown in FIG. 5. Bonded permanent magnets may also be used. Bonded magnets can be flexible or rigid, and consist of powdered NdFeB, Ferrite or SmCo permanent magnet materials bonded in a flexible or rigid substrate of e.g., silicone, rubber, nitrile, polyethylene, epoxy, polyvinyl chloride, or nylon. The forming of the bonded magnet can be achieved by extrusion, compression molding, injection molding, calendering, or printing. Bonded magnets enable unique flexible designs, and durable high tolerance shapes that are otherwise difficult to achieve.

In FIG. 5, the orientation of N-magnetic field is generally normal to the planar surface of the magnetic material 16 or 18, which is generally along the geometric z-axis (the geometric x-axis and y-axis laying within the plane of the magnetic material 16 or 18, as FIG. 5 shows).

Figure 6:
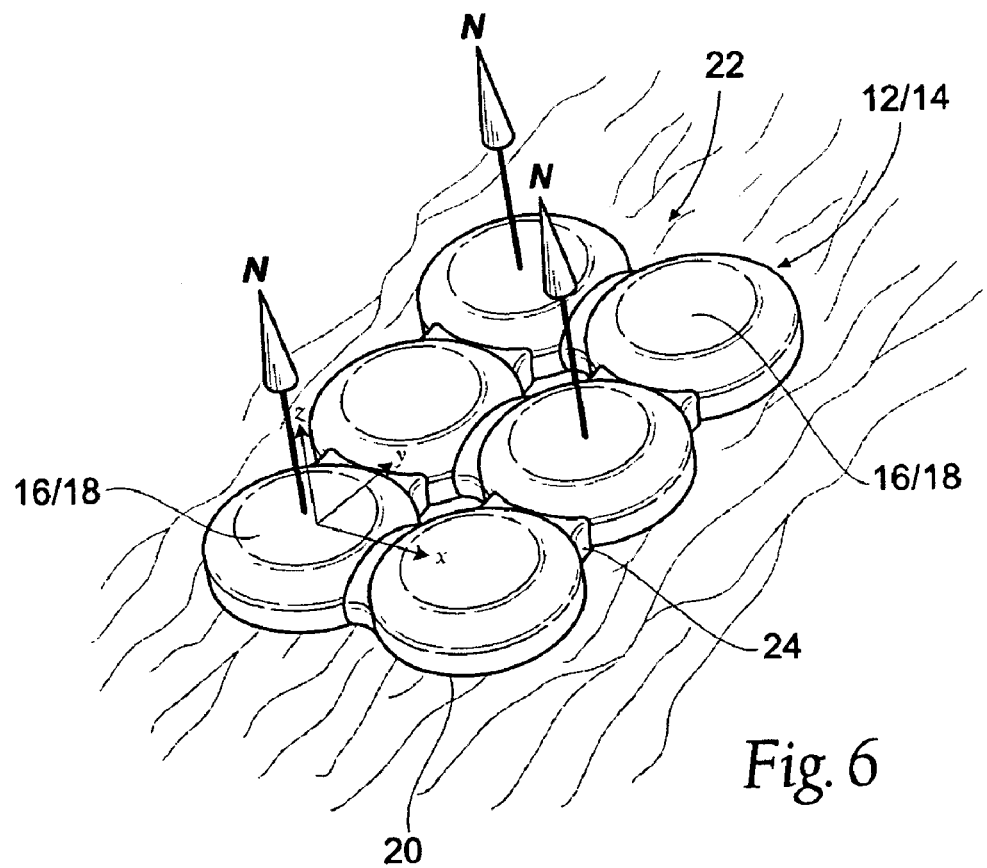
FIG. 6 shows an illustrative magnetic array implant.

Alternatively, a plurality of permanent magnetic material 16 or 18 can be positioned for implantation in a desirably flexible or compliant array 22 carried as a unit on a support carrier 24, or otherwise directly linked together, as shown in FIG. 6. The carrier 24 can comprise, for example, a woven, formed, or molded structure made, e.g., from a polymer or fiber or fabric or non-ferrous metallic material. Like the magnetic materials 16/18 themselves, the arrays 22 can be variously shaped, sized, and configured for implantation in the intended tissue region.

In the arrangement shown in FIG. 6, the magnetic materials 16/18 are placed on the carrier 24 with the N and S-poles facing generally in the same direction (which, in this embodiment, is generally along the z-axis). In FIG. 6, the N-pole orientation is shown by the arrows, and the S-pole is therefore oriented in an opposite direction. In this way, an array 22 of like permanent magnets 16/18 having the same magnetic orientation (i.e., polarity) can be assembled for implantation as a unit on the carrier 24.

In either arrangement (individually as shown in FIG. 5 or on an array as shown in FIG. 6), the magnetic material 16 or 18 is desirably coated, plated, encapsulated, or deposited prior to placement in or on tissue with a selected protective material 20. The protective material 20 is selected to provide a corrosion resistant and biocompatible interface, to prevent interaction between the magnetic material 16/18 and tissues/fluids of the body. The protective material 20 is also desirably selected to form a durable tissue interface, to provide longevity to the system component, and thereby provide resistance to structural fatigue and/or failure. Selected to provide these desired physical and physiologic benefits, the protective material 20 and its application to the material 16/18 is also desirably selected to avoid imparting added stiffness to the magnetic structure or magnetic component 12 or 14 itself.

The protective material 20 can be selected among various types of materials known to provide the desired biocompatibility, resistance to corrosion, and durability. For example, the protective material 20 can comprise titanium material plated, deposited, or otherwise coated upon the magnetic material 16/18. As another example, the protective material 20 can comprise a parylene coating. As other examples, the protective material 20 can comprise a silicone polymer, a non-toxic epoxy, a medical grade polyurethane, or a U.V. curable medical acrylic co-polymer. The protective material 20 may be made up of various layers, each contributing to the protective and/or biocompatibility characteristics of the protective material. The protective material 20 may also incorporate anticoagulants and/or antibiotics and/or tissue in-growth promoters.

C. Representative Systems of Magnetic Structures

Figure 7A:
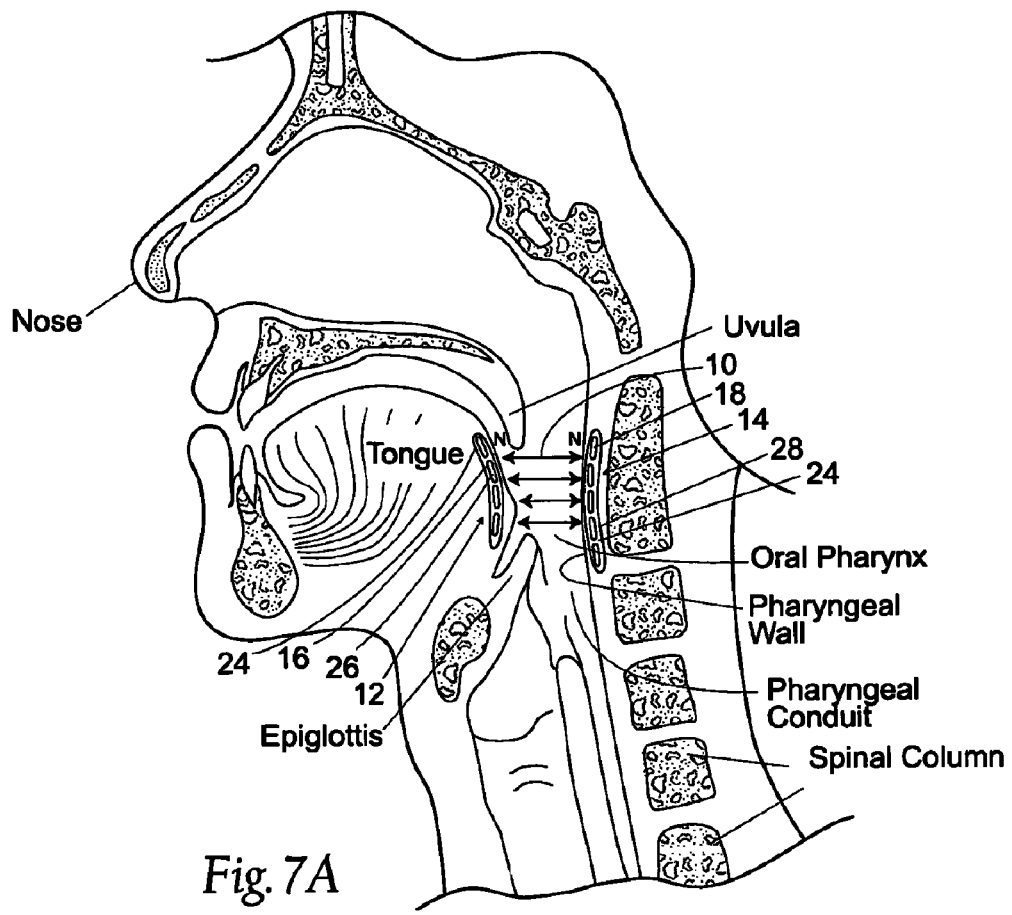
FIGS. 7A/B show a sagittal and a horizontal cross-sectional view of a human upper respiratory system comprising an illustrative repelling magnetic force system including a magnetic tongue implant and a pharyngeal wall implant.
Figure 7B:
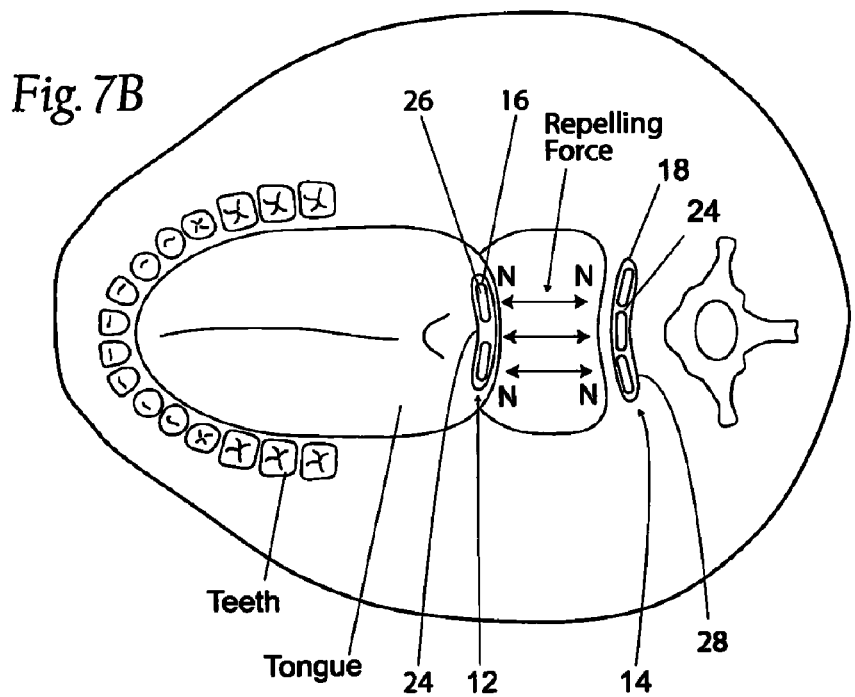

FIGS. 7A and 7B show a representative magnetic force system 10 comprising the magnetic materials 16 and 18 arranged in a repelling orientation, as previously described. In FIGS. 7A and 7B, the magnetic force system 10 includes a first magnetic structure or magnetic component 12 comprising a first magnetic array 26 implanted in the tongue. The magnetic force system 10 also includes a second magnetic structure or magnetic component 14 comprising a second magnetic array 28 implanted in a posterior pharyngeal wall.

As shown in FIGS. 7A and 7B, the arrays 26 and 28 each comprise a carrier 24, on which the magnetic materials 16 and 18 are arranged. As best shown in FIG. 7A, the carrier 24 is shaped along a longitudinal axis to have a length that is longer than its width. The longitudinally-shaped arrays 26 and 28 are implanted along the axis of the tongue and the airway, respectively.

At opposite end regions of each array 26 and 28, the array 26 and 28 includes the magnetic material (s), respectively 16 and 18. On each array 26 and 28, the N-S-poles of the magnetic materials 16 and 18 are oriented in the same direction, normal to the longitudinal axis. When implanted, as FIGS. 7A and 7B show, like poles of the magnetic material 16 of the first magnetic structure or magnetic component 12 are oriented to generally align with like poles of the magnetic material 18 of the second magnetic structure or magnetic component 14 across the airway, that is, either N-N or S-S-poles are generally aligned across the airway. As a result, the magnetic structure or magnetic component 12 in the tongue interacts by repelling the pharyngeal wall magnetic structure or magnetic component 14. A portion of the tissue in which the magnetic structures or magnetic components 12 and 14 are placed is therefore kept separated across the airway.

Figure 8A:
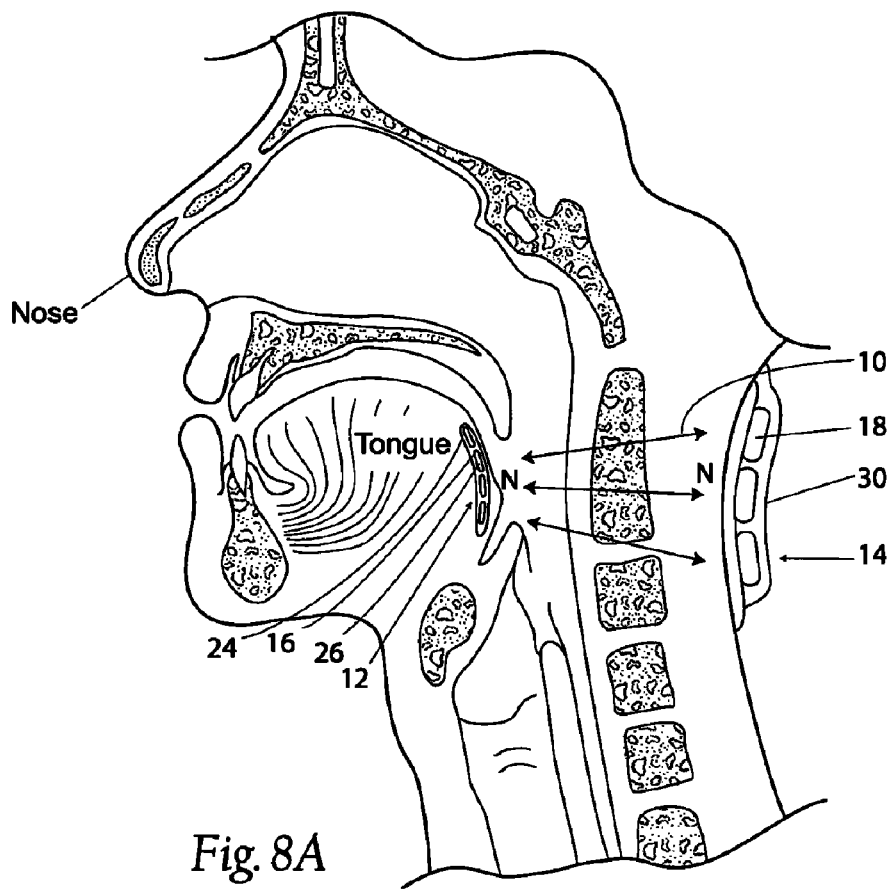
FIGS. 8A/B show a side view and a horizontal cross-section of a human upper respiratory system comprising an illustrative repelling magnetic force system including a magnetic tongue implant and an external magnetic source.
Figure 8B:
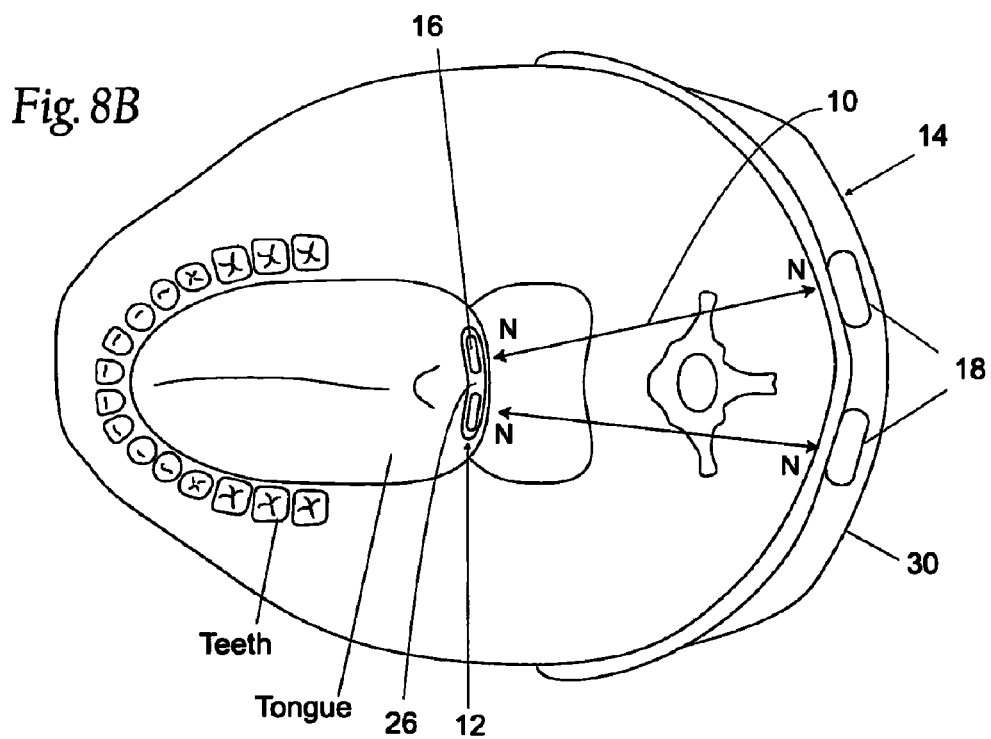

FIGS. 8A and 8B show another representative embodiment. In this embodiment, the first magnetic structure or magnetic component 12 in the tongue comprises a first magnetic array 26 arranged in a longitudinal carrier, like that shown in FIGS. 7A/B. In FIGS. 8A and 8B, however, the second magnetic structure or magnetic component 14 comprises a carrier 30, into which at least one magnetic material 18 is embedded. The carrier 30 comprises an external neck collar which is fitted for the neck of individual patients.

The first and the second magnetic structures or magnetic components 12 and 14 have the same polarity facing the airway. They magnetically interact by generating a magnetic repelling force between them. AS in the previous embodiment of the tongue and pharyngeal wall implants, the magnetic repelling force prevents a portion of the tongue from moving in a posterior direction and closing or restricting the pharyngeal conduit or airway.

In the embodiment shown in FIGS. 8A and 8B, the external carrier 30 can be worn about the neck at night to prevent apneic episodes during sleep. The external carrier 30 can be removed during the day, to remove the presence of the magnetic force field. The hybrid system shown in FIGS. 8A and 8B (partly implanted and partly external) can also be used as a trial or precursor to a fully implanted system, like that shown in FIGS. 7A and 7B. The size and configuration of the magnetic field can be titrated and assessed by altering the size and configuration of the external magnetic component 14—and, if necessary, the size and configuration of the first magnetic component 12—until a desired magnetic interaction between the components 12 and 14 is achieved. The relationship and resolution of the force or forces required to separate tongue from the posterior pharyngeal wall will be described in greater detail later, and the hybrid system shown in FIGS. 8A and 8B can be used to assess these force or forces on a trial basis, as well as assess an individual's tolerance to the presence of a magnetic field system. Once the magnetic force or forces have been titrated and assessed, and once an individual's tolerance or acceptance to the presence of a magnetic field system is ascertained, the external carrier 30 can be replaced by a magnetic component 14 (like that shown in in FIGS. 7A and 7B) placed in or on a posterior pharyngeal wall.

In both FIGS. 7A/B and 8A/B, the pharyngeal wall magnetic structure or magnetic component 14 provides one or more field direction(s) such that the pharyngeal implant maintains the repulsion as the tongue moves, e.g., during swallowing. However, the strength of the repelling force is not enough to interfere with the normal processes of swallowing, speaking, etc.

The various magnetic force systems 10 as described provide an elegant, cost-effective treatment of sleep apnea. Placed in or on tissue in the tongue and the pharyngeal wall, the magnetic structures or magnetic components 12 and 14 are well tolerated and are significantly more comfortable and user friendly than the equipment of CPAP or the highly intrusive surgical treatment options. The magnetic system 10 offers a sophisticated, yet easy to use design, which can be shaped, configured, and magnetically titrated to meet patients' individual needs, based upon specific anatomic requirements, as will be described in greater detail later.

III. Magnetic Structures for the Tongue

A. Magnetic Instability (Torque) in Repelling Magnetic Systems

Figure 10A:
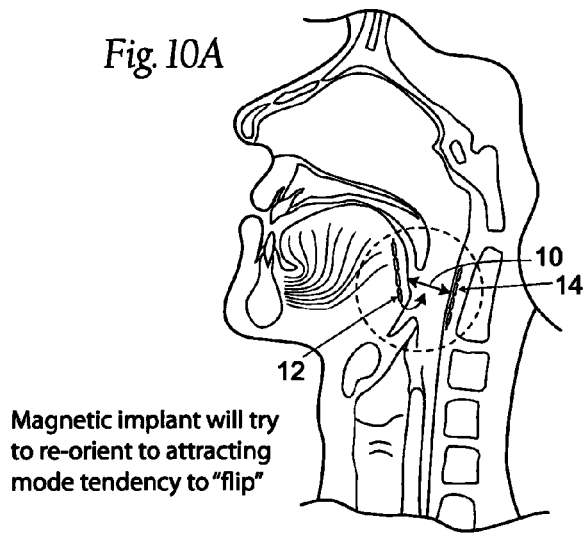
FIGS. 10A/B show an anatomical sagittal cross-sectional view of a human upper respiratory system as the tongue moves up with a repelling magnetic force system.
Figure 10B:
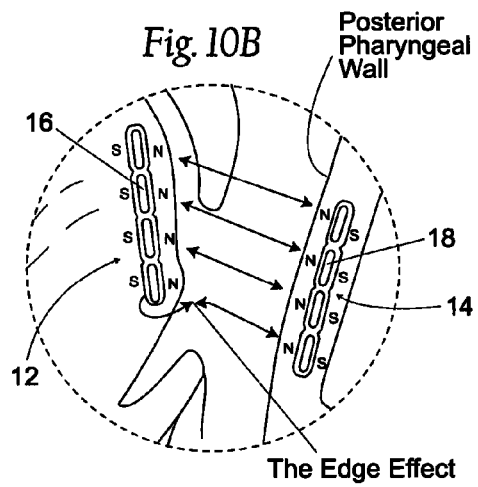
FIGS. 10C/D show a sagittal view of a human upper respiratory system as the tongue moves down with a repelling magnetic force system.
Figure 10C:
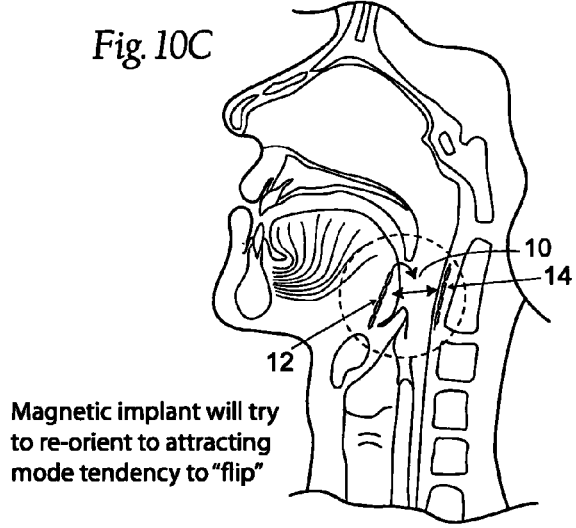
Figure 10D:
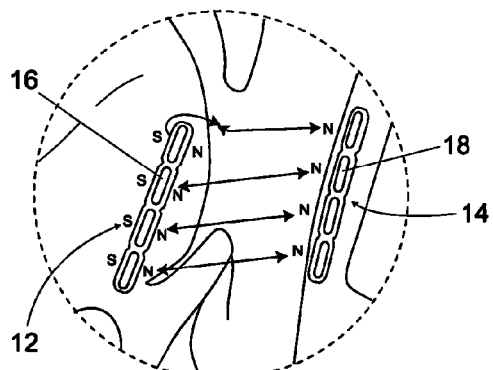

As shown in FIG. 9, the magnetic structures or magnetic components 12 and 14 are desirably generally aligned along the airway formed between the tongue and posterior pharyngeal wall to create a repelling magnetic force field. However, in reality, there is never a theoretically "perfect" magnetic alignment between the repelling magnetic materials 16 and 18. This is due to the anatomy of this region of the airway, coupled with the dynamic nature of the tongue itself. The orientation between the tongue and the pharyngeal wall varies due to the tongue's constant movement. There is rarely a geometrically "perfect," parallel relationship between the two tissue structures. Further, as FIGS. 10A and 10C show, when the tongue moves up and down, respectively, e.g., during swallowing, the movement can significantly alter the orientation and alignment between the repelling magnetic materials 16 and 18 from one moment to another.

From a purely physical standpoint, Earnshaw's theorem states that there is no possible static configuration in which repelling magnetic materials can achieve a stable state. [Earnshaw S. On the nature of the molecular forces which regulate the constitution of the luminiferous ether. Trans Camb Phil Soc 1842, 7:97-112.] According to Earnshaw's theorem, at the slightest misalignment from the "perfectly" magnetically aligned positions, two repelling magnets will start to move to position themselves in an attracting mode, because this is their lowest energy state. According to Earnshaw's theorem, repelling magnets that are not "perfectly" aligned will try to flip or twist into a non-repelling, attracting relationship, which is their lowest energy state. While torque is present in all systems, whether attracting or repelling, when repelling magnets are not in "perfect" alignment, where there is misalignment by angle or position, the decentering force and/or torque can increase rapidly.

For a more scientifically rigorous presentation of the above-mentioned material, Earnshaw's theorem states that there is no possible static stable configuration of objects subject to a combination of inverse square law forces. Such forces include gravity and magnetism, as applied to our product, but do not include stabilizing forces provided by the tongue. In essence, Earnshaw showed that inverse square law forces have no local minimum or maximum in their energy field, so they will always move, slide, and/or spin until they find a stabilizing force (generally when they are touching in attraction, which is the lowest energy state of a pair of magnets.) In our system, the tongue will provide stabilizing forces (which do not follow the inverse square law), to prevent this from happening. Variations in the force across an implant (or a magnet, or any other object) are interpreted as decentering forces and torques, and are present in any magnetic system that is not in perfect alignment.

Magnetic structures placed in or on mobile anatomic structures in the airway are seldom, if ever, orientated in a way that permits theoretically "perfect" alignment of repelling magnets. The alignment of the repelling magnetic materials is rarely "perfect," and it is subject to continuous change. It is by understanding and controlling the decentering and torque inherent in repelling magnetic systems, that the tongue can be effectively manipulated for the therapeutic purposes disclosed herein.

B. Design Considerations

Any repelling magnetic system involving the tongue desirably takes into account and balances three considerations: (i) one consideration is anatomic—it is the lack of perfect parallel alignment between the tongue and the pharyngeal wall in the airway, which is compounded by the natural movement of the tongue relative to the pharyngeal wall, (ii) the other consideration is physical—it is the torque and decentering force that the interaction of repelling magnetic forces creates in systems where less than perfect alignment occurs and the ability of movable structures in the airway to resist those forces, as explained by Earnshaw's theorem, and (iii) the third consideration is the ability to place implants or variability in placement of implants in the most desired orientation to one another.

A given repelling tongue implant should desirably be maintained predominantly in a position of repulsion (and not attraction) as other structures, such as the tongue, move in relation to the pharyngeal wall. For example, it should be recognized that during the process of chewing and swallowing, the tongue undergoes a wide variety of motions and changes of angular orientation to the pharyngeal wall.

A given tongue implant desirably includes features for maintaining the implant in its predominantly repelling state at all the angular alignments normally and abnormally encountered with respect to the pharyngeal wall but should still allow for normal performance of natural bodily functions such as swallowing and speech.

C. The Edge Effect

We have discovered that maintaining implants in a repelling position with respect to each other desirably gives particular attention to magnetic forces that are generated at the edges of the implant. As FIGS. 10A and 10C demonstrate, as soon as the edges of the implants (initially repelling) start to misalign, the magnets at the edges of the implant may start to twist in an attempt to orient themselves to more desired attracting arrangement. This can cause an implant to twist, flip, and sometimes even close the pharyngeal conduit.

For example, FIG. 9 shows the N-pole of the magnetic structure or magnetic component 12 initially oriented in an alignment with respect to the repelling N-pole of the pharyngeal wall magnetic structure or magnetic component 14 that is conducive to repelling. However, as FIGS. 10A and 10C show, as the tongue naturally moves up and back, or when it abnormally collapses during an apneic episode, the N-pole of the magnets on an edge region of the tongue implant 12 can come out of the existing beneficial alignment with the N-pole of the magnets on the pharyngeal wall magnetic structure or magnetic component 14. As alignment changes, the S-pole of magnets on the tongue implant 12 can move progressively into attracting alignment with the N-pole of the magnets of the pharyngeal wall magnetic structure or magnetic component 14 (FIG. 10C). Torquing and attracting forces are generated by this misalignment (as a corollary to Earnshaw's theorem). As a result, the tongue implant 12 may start to flip to move into a position of lower repulsion and/or attraction with respect to the pharyngeal wall magnetic structure or magnetic component 14.

To overcome and control these decentering and twisting tendencies, which also takes into account the anatomic and physical considerations described above, an implant desirably manipulates and adjusts the nature of the magnetic fields in certain regions of the implant, particularly along one or more edges of the implant. The manipulation and adjustment of the magnetic fields makes certain that, even though some of magnetic poles are not in or may fall out of "perfect" repelling alignment with another magnet, there will be at least some magnetic poles that are maintained in a repelling alignment sufficient to resist twisting or flipping the entire implant.

D. Angled Magnetic Fields

In one arrangement, the flipping and twisting tendencies can be overcome or at least controlled by the inclusion of magnetic fields that are mutually angled within the implant and/or along one or more ends of the implant. The angling of magnetic fields makes certain that even though some of magnetic poles may fall out of repelling alignment with another magnet, there will be at least some magnetic poles that are maintained in a repelling alignment with respect to repelling magnetic poles of the other magnet.

Figure 11:
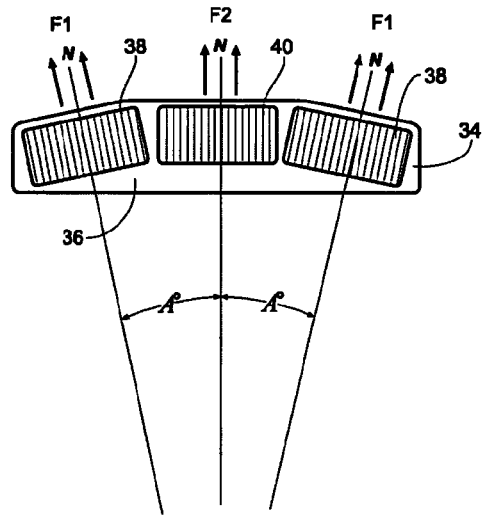
FIG. 11 shows an illustrative magnetic implant with angled magnetic fields.

FIG. 11 shows a representative magnetic implant 34 sized and configured for implantation in a tongue that embodies this feature. The implant 34 comprises a carrier structure 36 sized and configured for placement in or on tissue. The implant 34 includes at least two sources 38 and 40 of magnetism carried by the carrier structure 36. Each source 38 and 40 generates a magnetic force field, shown in FIG. 11 as a first force field F1 and a second force field F2, respectively. The sources 38 and 40 can each comprise a permanent magnet, as previously described.

As FIG. 11 shows, the first and second force fields F1 and F2 have a direction. The magnetic force fields F1 and F2 each comprises either a north polarity N or a south polarity S, as previously described. In FIG. 11, the force fields comprise a north polarity N. The first and second force fields F1 and F2 of the implant 34 have the same polarity; that is, they are either both N-poles or both S-poles. In FIG. 11, they are both N-poles. This arrangement is consistent with the configuration of implants previously described.

However, unlike the previously-discussed implants, in the implant 34 shown in FIG. 11, the direction of the first magnetic force field F1 is orientated at an angle A from the direction of the second magnetic force field F2. It is this angularity between or among the plurality of force fields F1 and F2 of the implant 34, particularly when placed at one or more edges of the implant 34, that keeps the implant 34 from flipping or twisting in a repelling force field that is not in perfect alignment with another repelling implant and/or that is subject to change in alignment in response to the natural movement of anatomic structures.

The angularity (i.e., the magnitude of angle A) can be selected empirically based upon general anatomic considerations for a population of individuals, or the angularity can be customized for a given implant according to the anatomic configuration of a particular individual's tongue. In this arrangement, the individual undergoes fluoroscopy to image the individual's tongue. Based upon the images of the tongue, the clinician can assess the morphology of the tongue and determine a desirable angularity of the magnetic fields of the tongue implant 34. In this way, based on the individual's particular anatomical requirements, a magnetic tongue implant with angled magnetic fields can be assembled and implanted. It has been discovered that, for a tongue implant the angle A is desirable at least 10 degrees.

In FIG. 11, the angularity between the force fields F1 and F2 is achieved by physically orienting the pole direction of the source 38 to face a different direction than the pole of the source 40. In the arrangement, the carrier structure 36 possesses a generally planar configuration prior to implantation.

Figure 12A:
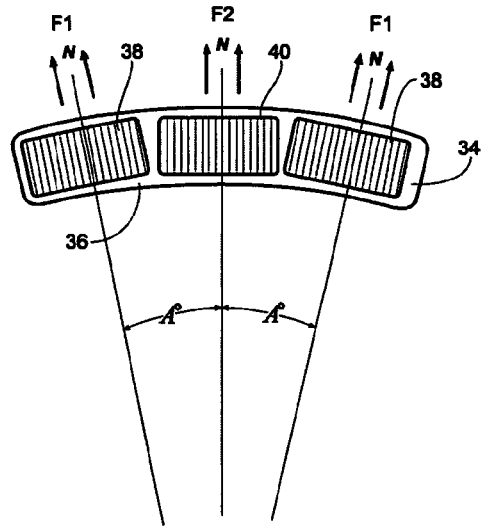
FIGS. 12 A/B/C show alternative embodiments for magnetic implants with angled magnetic fields.

In FIG. 12A, the angularity between the force fields F1 and F2 is achieved by physically orienting the pole direction of the source 38 to face the same direction as the pole of the source 40, and by flexing the carrier structure 36 to form the requisite angle A. The flexure can comprise a preformed curve, as shall be explained later, or the flexure can occur during implantation, as the carrier structure conforms to the curve morphology of the tongue itself.

Figure 12B:
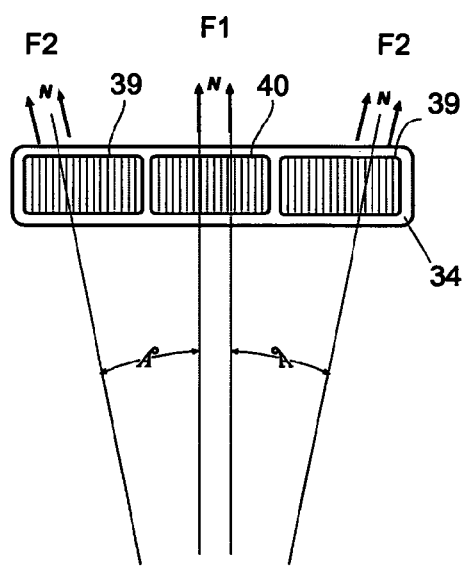
Figure 12C:
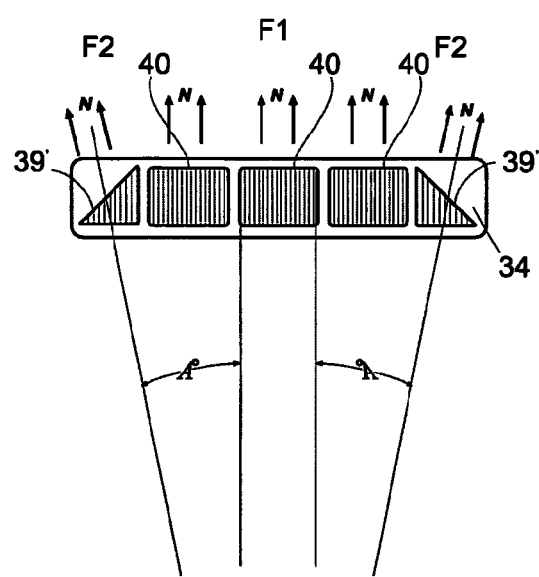

In FIG. 12B, the angularity between the force fields F1 and F2 is achieved by angling the magnetic field of the source 39 at and angle A with respect to the direction of the magnetic field source 40. FIG. 12C is an alternative to FIG. 12B. The source 39' comprises wedge magnets and the angularity between the force fields F1 and F2 is achieved by angling the magnetic field of the source 39' at and angle A with respect to the direction of the magnetic field source 40.

Figure 13A:
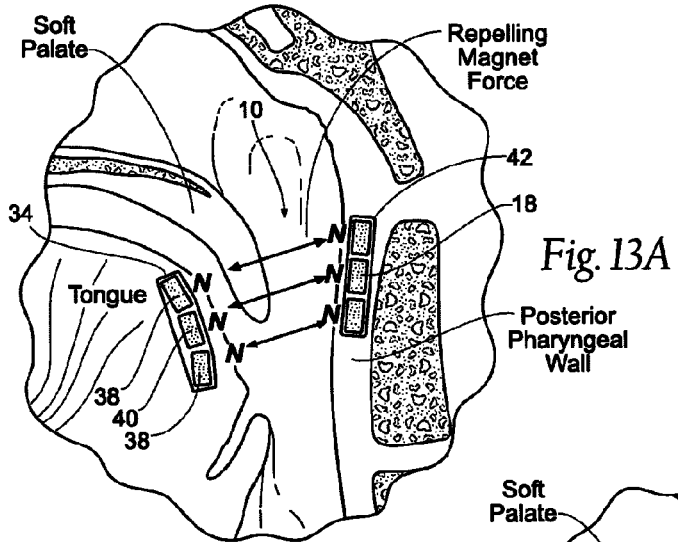
FIGS. 13A/B/C and 14A/B/C are anatomical sagittal views of human upper respiratory systems showing embodiments of angled magnetic field implants in repelling magnetic force systems.
Figure 13B:
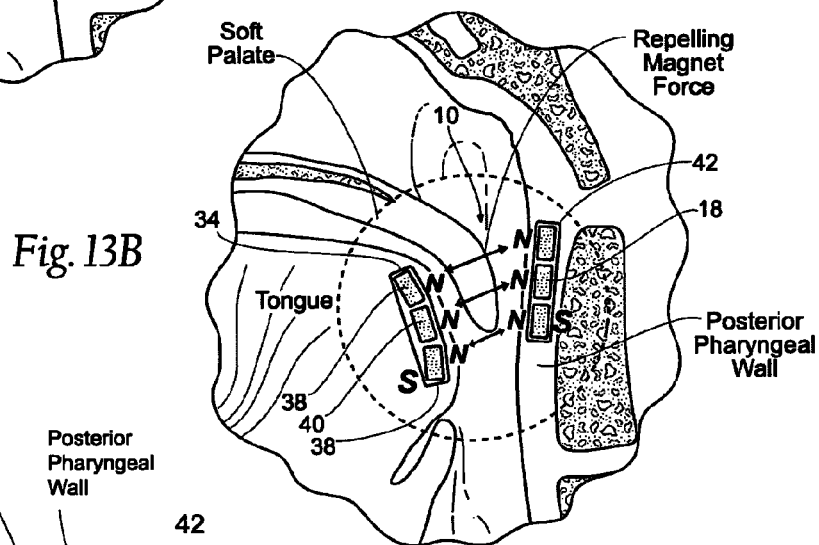
Figure 13C:
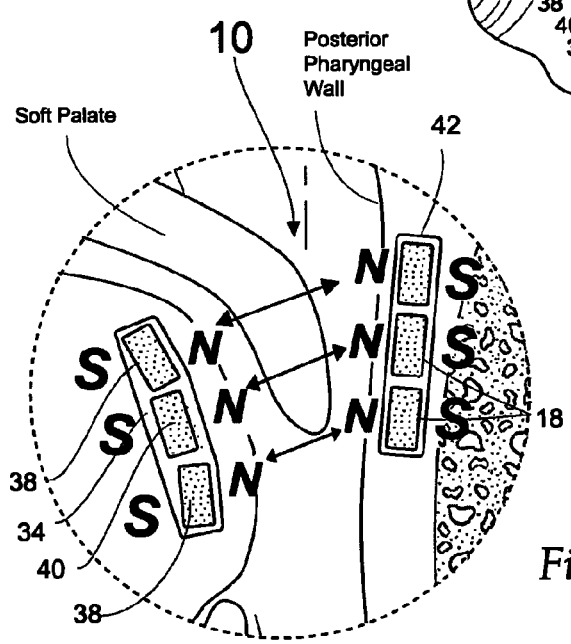

FIGS. 13A/B/C and 14A/B/C show embodiments of a magnetic force system 10, which includes a magnetic implant 34 of the type shown in FIGS. 11 and 12A/B/C (respectively). The magnetic implant 34 is implanted in the tongue in an anterior-to-posterior direction. The magnetic implant 34 magnetically repelling a second magnetic implant 42, which is implanted in a posterior pharyngeal wall in a superior-to-inferior direction.

In FIGS. 13A/B/C and 14A/B/C, the implants 34 and 42 each includes a plurality of magnetic materials, respectively 38/40 (corresponding to what is shown in FIGS. 11 and 12) and 18. The N-poles of the magnetic materials 38/40 and 18 are oriented to generally align with each other across the airway, forming an adequate repelling relationship, albeit not "perfect" in a physical sense.

The directions of the force fields of the N-poles of pharyngeal wall implant 42 are generally the same, being normal to the pharyngeal wall implant 42 and hence normal to the pharyngeal wall. However, the direction of at least one of the N-pole magnetic force fields of the palate implant 34 is orientated at an angle of desirably at least 10-degrees from the direction of another N-pole magnetic force field on the palate implant 34. In FIGS. 13A/B/C, a generally planar implant as shown in FIG. 11 is implanted, in which the angularity is achieved by orienting the pole of at least one magnet 38 differently than the pole or poles of other magnets 40. In FIGS. 14A/B/C, a curved implant 34 as shown in FIG. 12 is implanted, in which the angularity between the magnets 38 and 40 is achieved by virtue of the curve of the implant carrier.

Angling the magnetic field of at least one magnet in the tongue implant 34, using an angle A that is determined empirically allows at least one magnet of the magnetic tongue implant 34 to remain in repelling alignment with at least one magnet in the magnetic pharyngeal wall implant 42, regardless of any particular anatomic misalignment due to the configuration of the tongue and changes in the angular alignment between the pharyngeal wall and the moving tongue. The implant 34 therefore enhances the intended function of the implant 34 in keeping the pharyngeal airway open. Even should the tongue collapse during sleep, the angling of the magnetic field(s) of the tongue magnet(s) maintains the predominantly repelling interaction of the tongue implant 34 and the pharyngeal wall implant 42, thus preventing apneic events.

E. Radial Magnetic Fields

A radial magnet is a magnet whose internal magnetic polarization changes direction along one or more of its dimensions. More generally, magnets may be constructed with variable (magnetic) field directions.

FIG. 15A shows a magnetic tongue implant 44 comprising a carrier structure 46 sized and configured for placement in or on tissue. The implant 44 includes at least two sources 48 and 50 of magnetism carried by the carrier structure 46. At least one of the sources 48 and 50 comprises a permanent magnet 52 with radial magnetization. The magnetic flux field of the radial magnet 52 extends radially from the center of the magnet, as shown by arrows in FIG. 15A. The permanent radial magnet 52 presents the same magnetic pole (north or south) about its entire outer surface. The presence of the radial magnet 52 may be desirable, particularly on the lower edge of a tongue implant 44, because the radial flux field can overcome problems associated with flipping due to attraction at the edges of the implants.

Alternatively, as seen in FIG. 15B, at least one of the sources 48 and 50 comprises a permanent magnet with variable magnetic field direction 52'. The magnetic flux field of the variable field direction magnet 52' extends in variable directions from the center of the magnet, as shown by arrows in FIG. 15B. The permanent variable field direction magnet 52' presents a varying magnetic pole (north or south) about its outer surface. The presence of the variable field direction magnet 52' may be desirable, particularly on the lower edge of a tongue implant 44', because the variable direction flux field can also overcome problems associated with flipping due to attraction at the edges of the implants.

FIGS. 16A/B/C show a magnetic force system 10 comprising the magnetic tongue implant 44 shown in FIG. 15 used in association with magnetic pharyngeal wall implant 54. The poles of the magnet 50 on the magnetic tongue implant 44 and the magnets 18 of the pharyngeal wall implant 54 are alike across the airway (N-N or S-S), thus repelling each other. As before described, a tongue implant 44 can undergo extensive bending in the process of swallowing. Thus the magnets along the lower edge of the tongue implant 44 are prone to come out of alignment with respect to the magnets in the pharyngeal wall implant 54. As before described, absent the presence of a radial or variable field direction magnet 52/52', the lower edge magnets may have a greater tendency to twist to re-direct themselves into an attracting position.

As shown in FIGS. 16B/C, the presence of the radial or variable field direction magnet 52/52' in the implant 44 resists this effect. As seen in FIGS. 16B/C, when the tongue moves during the process of swallowing, the magnetic field generated by radial or variable field direction magnet 52/52' keeps the lower edge of magnetic tongue implant 44 from twisting and re-directing itself into an attracting position with respect to magnetic pharyngeal wall implant 54. The magnetic field generated by radial or variable field direction magnet 52/52' maintains magnetic tongue implant 44 in a predominantly repelling position even as the tongue moves.

Figure 16D:
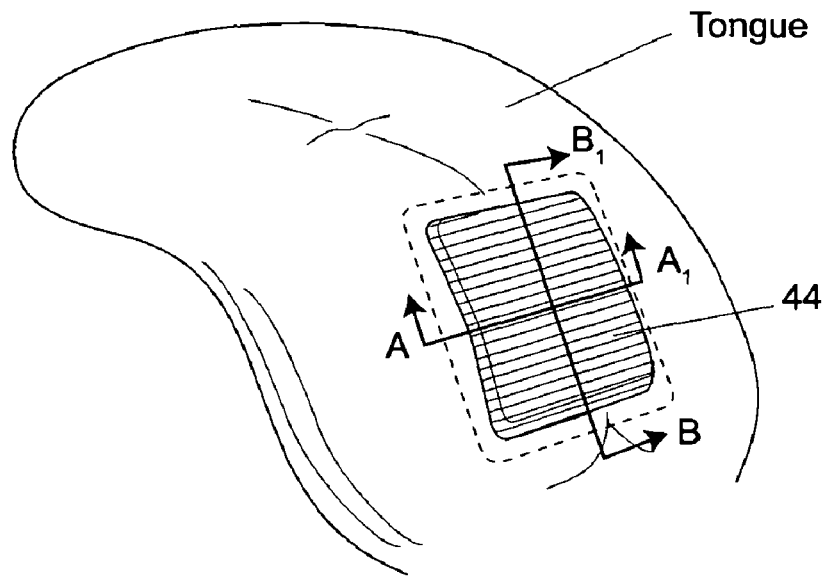
FIG. 16D shows a human tongue with an implanted magnetic tongue implant.
Figure 16E:
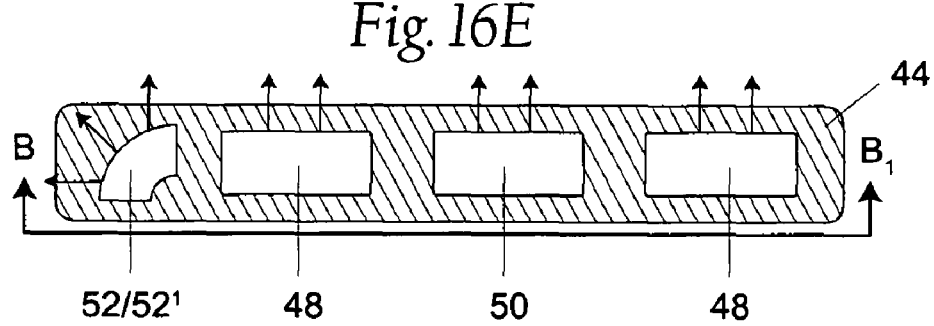
FIGS. 16A/B/C are anatomical sagittal views of a human upper respiratory system showing a magnetic tongue implant with radial or variable magnetic field direction magnets in a repelling magnetic force system.
FIGS. 16/E/F are longitudinal cross sections of magnetic tongue implants comprising radial magnets or variable magnetic field direction magnets.
Figure 16F:
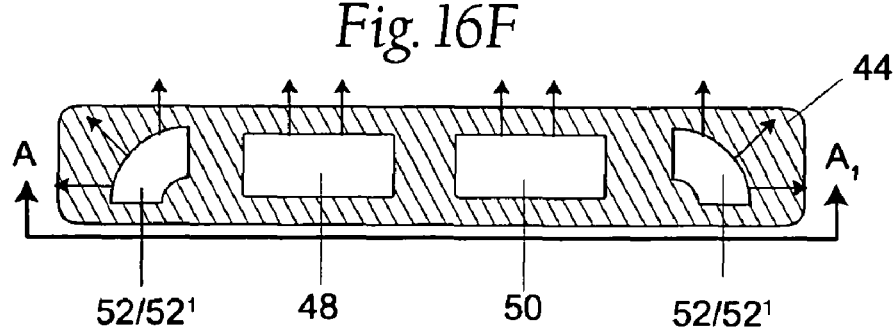

FIG. 16D shows the positioning of magnetic implant 44 in a tongue. FIG. 16E is a cross-section along the length (B-B1) of the magnetic implant 44. As can be seen in FIG. 16E the radial or variable field direction magnet 52/52' is located in the caudal position at the base of the tongue. FIG. 16F shows a cross-section along the width (A-A1) of the magnetic implant 44. As can be seen in FIG. 16F, radial or variable field direction magnets 52/52' are located along both of the lateral edges of magnetic implant 44. The radial or variable field direction magnets 52/52' prevent the magnetic implant 44 from becoming destabilized when the tongue moves from the generally aligned position, thus preventing the tongue from twisting.

F. Curvature and Adaptability of Shape

Figure 17A:
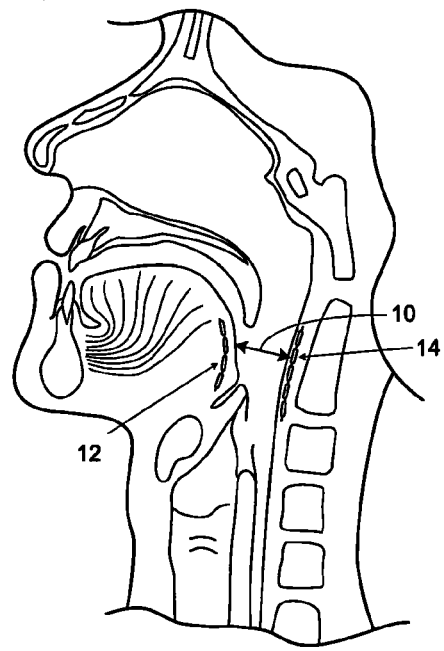
FIGS. 17A/B/C are anatomical sagittal views of a human upper respiratory system showing a curved magnetic tongue implant in a repelling magnetic force system.
Figure 17B:
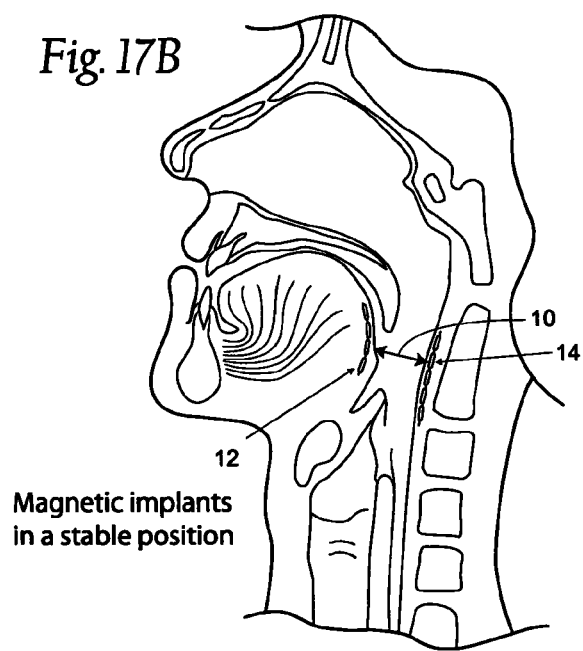
Figure 17C:
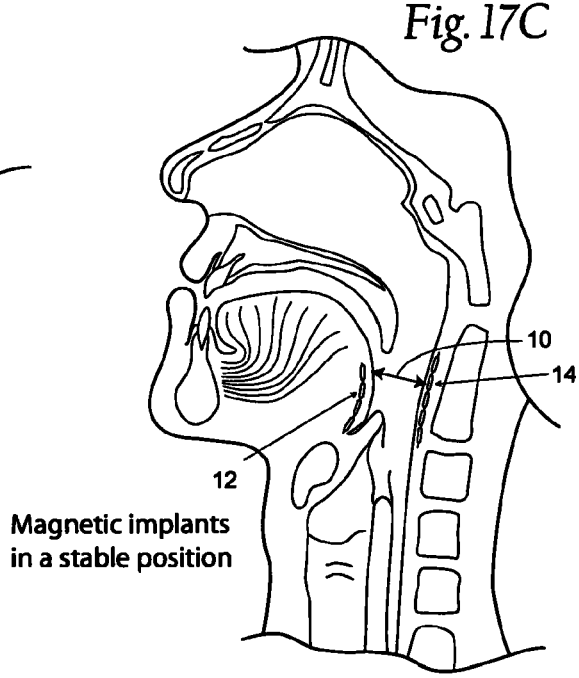

To mediate the previously-described decentering, twisting or flipping of the tongue implant, curvature is added along the length of the implant. The curvature in the implant insures that, throughout the natural (cranial, caudal, posterior, anterior, lateral, or rolling) motion of the tongue with respect to the pharyngeal wall, there will always be a sufficient number of magnets that are in a repelling state with respect to the magnets in the pharyngeal wall implant. This curvature also allows the implant to follow the natural shape of the tongue and not hinder its natural movement in speech, swallowing, etc. FIGS. 17A/B/C show how curved tongue implants maintain a repelling magnetic interaction when the tongue is in a level position (FIG. 17A); moves up (FIG. 17B); or moves down (FIG. 17C).

Figure 18A:
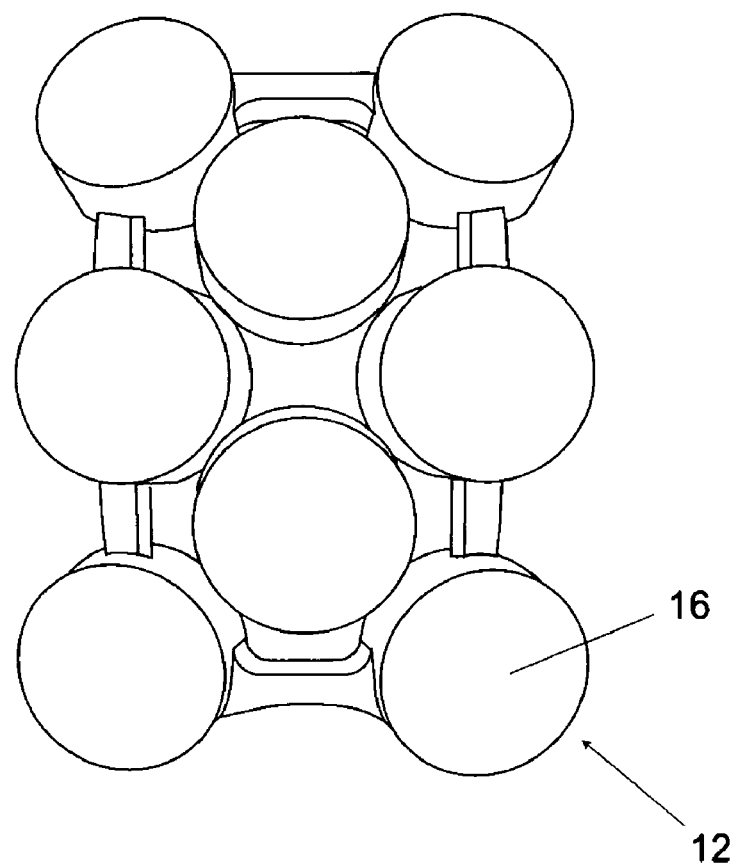
FIGS. 18A/B show a front view and a latitudinal side view of a curved magnetic tongue implant.
Figure 18B:
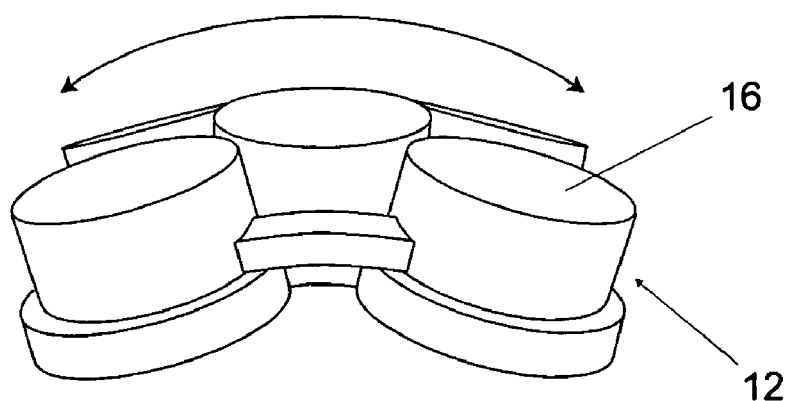

Furthermore, the tongue is a very strong muscle. Should an implant prevent its natural position and/or movement, then, most likely the large force of the tongue will inappropriately bend, pull, or otherwise deform, and/or attempt to move the implant. This relative implant to adjacent tissue motion can lead to extrusion of the implant. Thus, to encourage a symbiotic relationship between the tongue implant and the tongue, curvature is desirably added along either the length, or the width of the implant, or both, as shown in FIGS. 18A/B. This feature allows the tongue and the implant to move together in a natural manner.

Figures 19A, 19B:
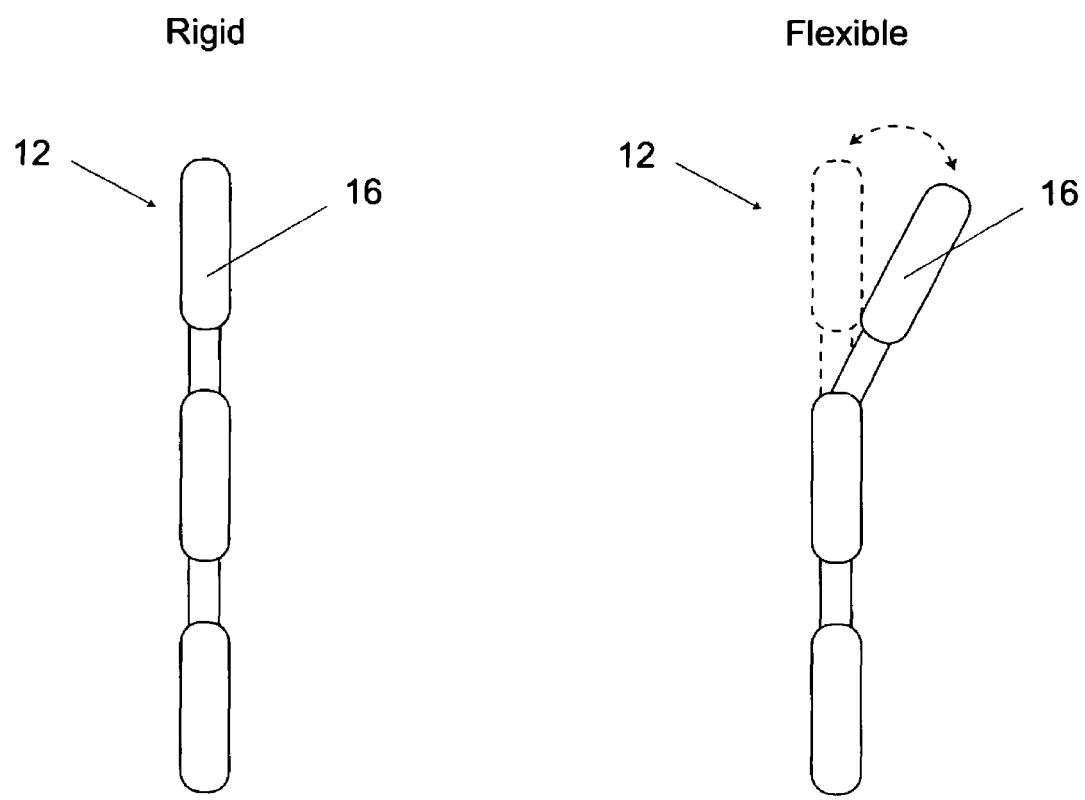
FIGS. 19A/B show a longitudinal side view of a magnetic tongue implant in a non-flexible and a flexible matrix, respectively.

Another desirable feature of the magnetic tongue implant is the matrix's inherent ability to change its shape or flex in response to the repelling force pivoting the attracting outside edge of the implant away from the opposing repelling implant and maintain the highest predominantly repelling energy state and prevent movement to attraction. The implant structure is specially designed to allow this flexure to take place. FIG. 19A shows magnetic structure or magnetic component 12 in a regular non-flexible matrix; in this case the magnetic component is only able to pivot. FIG. 19B shows magnetic component in a flexible matrix that encourages movement of the implant so as to maximize repelling forces. This adaptability of shape can also apply to implants which accommodate the natural motion of the structures of the airway (i.e. the tongue or pharyngeal walls).

Figure 20A:
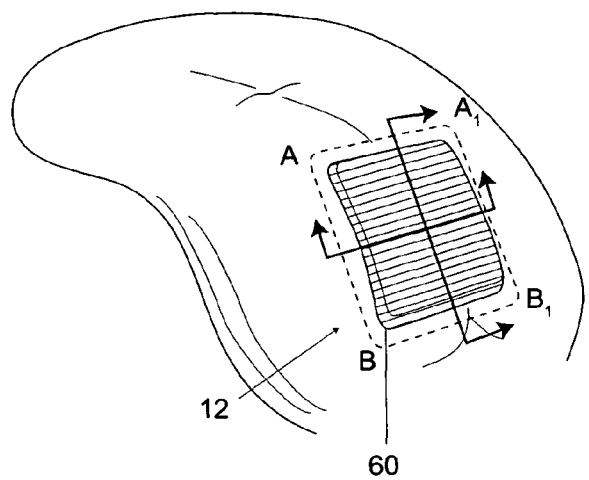
FIG. 20A shows a human tongue with an implanted magnetic tongue implant.
Figure 20B:
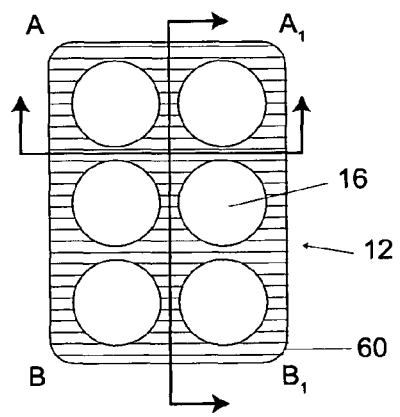
FIGS. 20B/C/D show a frontal view, a latitudinal cross-section, and a longitudinal cross-section of the magnetic tongue implant.
Figure 20C:
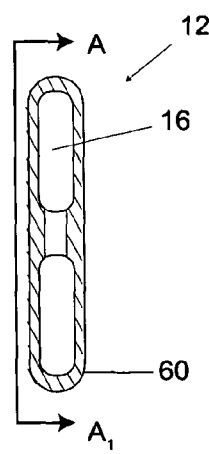
Figure 20D:
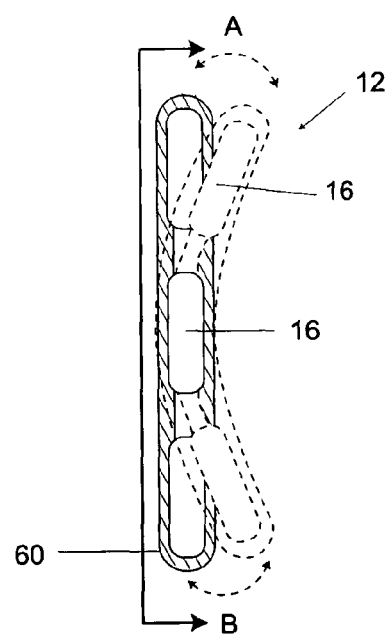

The implant must be sufficiently flexible so as not to impair the normal functions of the tongue, such as swallowing, or speech; it must also be rigid enough to withstand folding on itself, due to the interactions of multiple magnets within the structure or forces placed on the implant by the tongue or other airway structure. Tongue implants must strike a balance between having enough rigidity to maximize their therapeutic effect in treating sleep disordered breathing and adequate flexibility to prevent the implant's interference with the normal function of the muscles covering it. Implants can also be designed so as to allow flexibility in one place to accommodate tongue bending, while having rigidity in another so as to maintain a therapeutic effect. FIG. 20A shows magnetic structure or magnetic component 12 implanted in the tongue. Magnetic structure or magnetic component 12 comprises a magnetic tongue implant 60. FIG. 20B shows the four corners A, A', B, and B' of magnetic tongue implant 60. FIG. 20C is a horizontal cross-section (A-A') of magnetic tongue implant 60; as can be seen from this figure, magnetic tongue implant 60 is rigid in the horizontal direction. FIG. 20D is a vertical cross-section (A-B) of magnetic tongue implant 60; as can be seen from this figure, magnetic tongue implant 60 is flexible in the vertical direction.

G. Illustrative Examples of Curved and Shape Adaptable Implants

Figure 21:
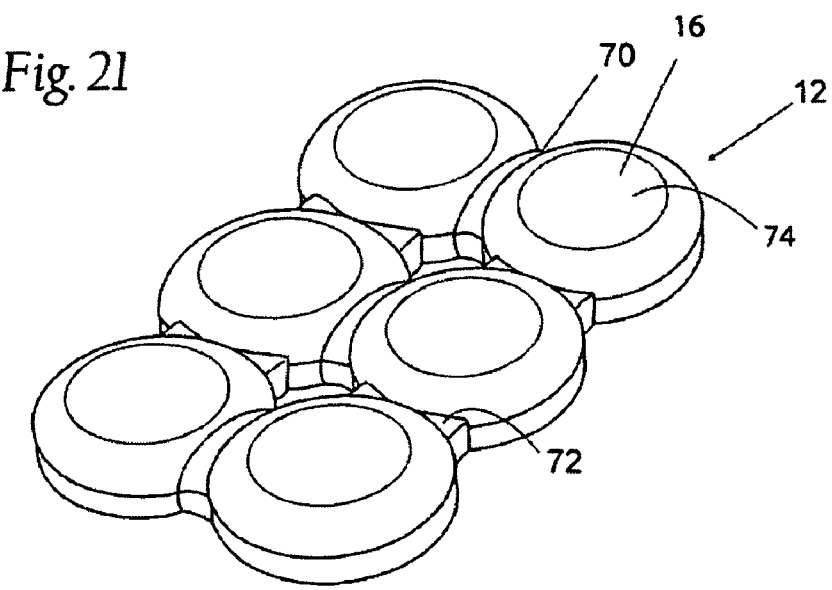
FIGS. 21/22/23/24/25/26 show alternative embodiments of magnetic tongue implant arrays.

FIG. 21 shows an embodiment of the original magnetic structure or magnetic component 12. Magnetic structure or magnetic component 12 comprises a magnetic tongue implant 70. Magnetic tongue implant 70 comprises a flat, flexible structure 72 and six magnets 74 therein embedded. The structure allows the implant to flex to accommodate the repelling force and prevent movement to attraction. Magnetic structure or magnetic component 12 interacts with magnetic structure or magnetic component 14 in the pharyngeal wall, by repelling.

Figure 22:
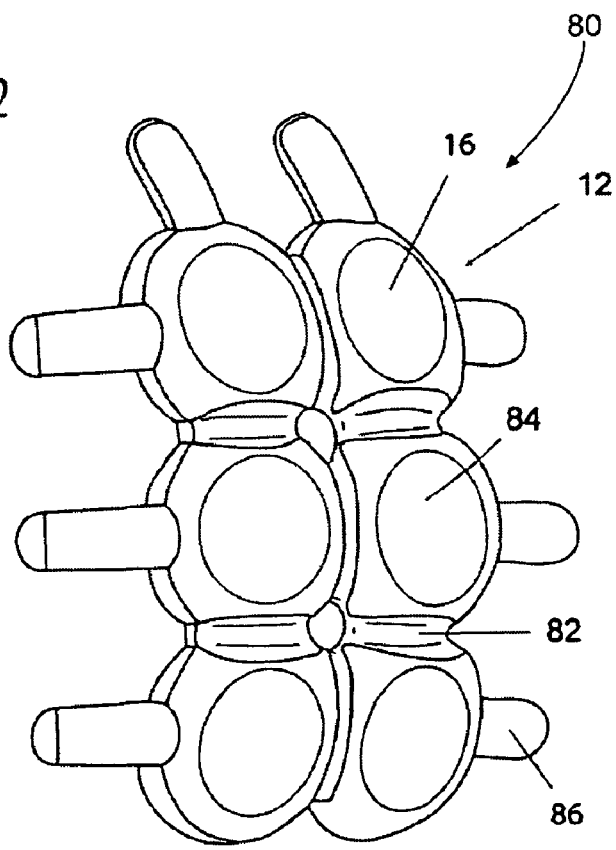

FIG. 22 shows an alternative embodiment of the magnetic structure or magnetic component 12. Magnetic tongue implant 80 comprises a flat, flexible structure 82 and six magnets 84 therein embedded. The flexible structure 82 is curved along the length of the magnetic tongue implant. The curvature permits the implant to maintain itself in a repelling state with respect to magnetic structure or magnetic component 14 in the pharyngeal wall or externally, i.e. in a neck collar, over a wider angle/range than if the magnetic tongue implant were straight. Furthermore, magnetic implant 80 comprises integrated tabs 86 that extend outward from the magnetic discs to engage adjacent tissue and provide enhanced stabilization for the tongue.

FIG. 23 shows an alternative embodiment of the magnetic structure or magnetic component 12. Magnetic structure or magnetic component 12 comprises a magnetic tongue implant 90. Magnetic tongue implant 90 comprises a flexible structure 92 and eight magnets 94 therein embedded. The flexible structure 92 is curved along both the length and the width of the magnetic tongue implant. The curvature permits the implant to maintain itself in a repelling state with respect to the pharyngeal wall magnetic structure or magnetic component 14 over a wider angle/range both along the length and the width of the tongue than if the magnetic tongue implant were straight.

FIG. 24 shows an alternative embodiment of the magnetic structure or magnetic component 12. Magnetic structure or magnetic component 12 comprises a magnetic tongue implant 100. Magnetic tongue implant 100 comprises a flexible structure 102 and eight magnets 104 therein embedded. The flexible structure 102 is curved along both the length and the width of the magnetic tongue implant. The curvature permits the implant to maintain itself in a repelling state with respect to magnetic structure or magnetic component 14 in the pharyngeal wall over a wider angle/range both along the length and the width of the tongue than if the magnetic tongue implant were straight. Furthermore, magnetic implant 100 comprises integrated tabs 106 that extend outward from the magnetic discs to engage adjacent tissue and provide enhanced stabilization for the tongue.

FIG. 25 shows an alternative embodiment of the magnetic structure or magnetic component 12. Magnetic structure or magnetic component 12 comprises a magnetic tongue implant 110. Magnetic tongue implant 110 comprises a flexible structure 112 and eleven magnets 114 therein embedded. The flexible structure 112 is curved along both the length and the width of the magnetic tongue implant. The curvature permits the implant to maintain itself in a repelling state with respect to magnetic structure or magnetic component 14 in the pharyngeal wall over a wider angle/range both along the length and the width of the tongue than if the magnetic tongue implant were straight. Magnetic tongue implant 110 offers a particularly effective alternative to patients whose anatomical structure requires a longer tongue implant for effective therapeutic effects.

FIG. 26 shows an alternative embodiment of the magnetic structure or magnetic component 12. Magnetic structure or magnetic component 12 comprises a magnetic tongue implant 120. Magnetic tongue implant 120 comprises a flexible structure 122 and eleven magnets 124 therein embedded. The flexible structure 122 is curved along both the length and the width of the magnetic tongue implant. The curvature permits the implant to maintain itself in a repelling state with respect to magnetic structure or magnetic component 14 in the pharyngeal wall over a wider angle/range both along the length and the width of the tongue than if the magnetic tongue implant were straight. Furthermore, magnetic implant 120 comprises integrated tabs 126 that extend outward from the magnetic discs to engage adjacent tissue and provide enhanced stabilization for the tongue. Along with magnetic tongue implant 110, magnetic tongue implant 120 also offers a particularly effective alternative to patients whose anatomical structure and relative movement requires a longer tongue implant for effective therapeutic effects.

H. Stabilization

Figure 27A:
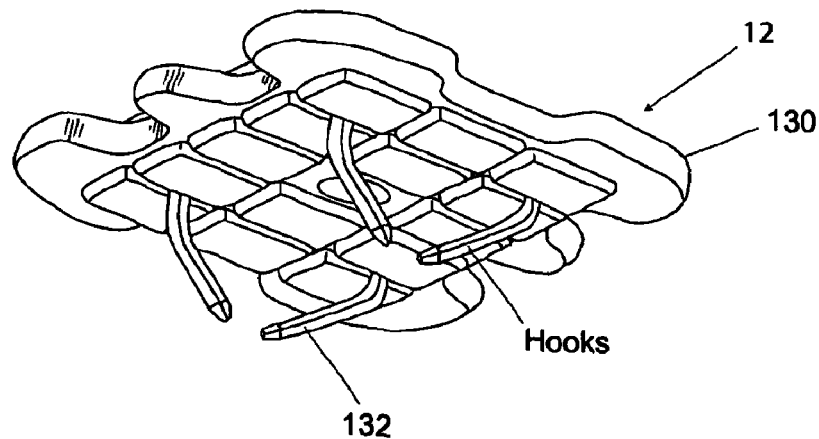
FIGS. 27A/B/C/D/E/F/G/H show magnetic tongue implants comprising various means of controlling implant movement and migration in the tongue.

Any implant in the tongue has the potential to migrate or move to a magnetically less repelling or attractive position because the tongue is a structure that, due to its function, moves in all directions. Such movement or migration needs to be controlled using various means. FIGS. 27A/B/C/D/E/F/G/H show magnetic tongue implants comprising various means of controlling implant movement or migration in the tongue.

Figure 27B:
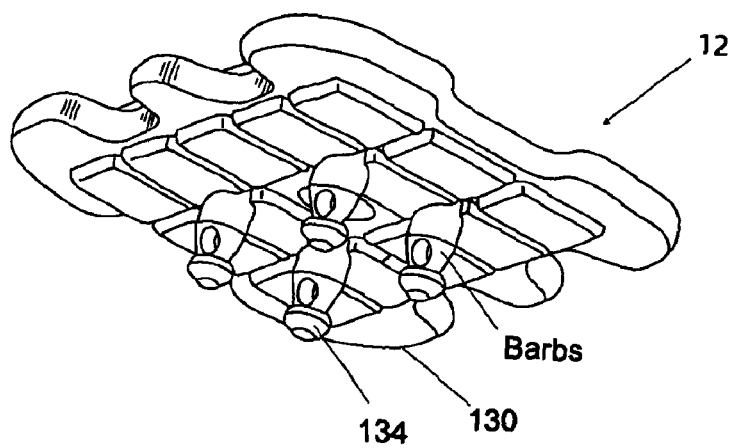

For example, magnetic tongue implants 130 may be anchored to tongue tissue using hooks 132 (see FIG. 27A), or barbs 134 (see FIG. 27B). The hooks and barbs will grab the top tissue and limit motion, thus preventing migration and the folding of the implant upon itself.

Figure 27C:
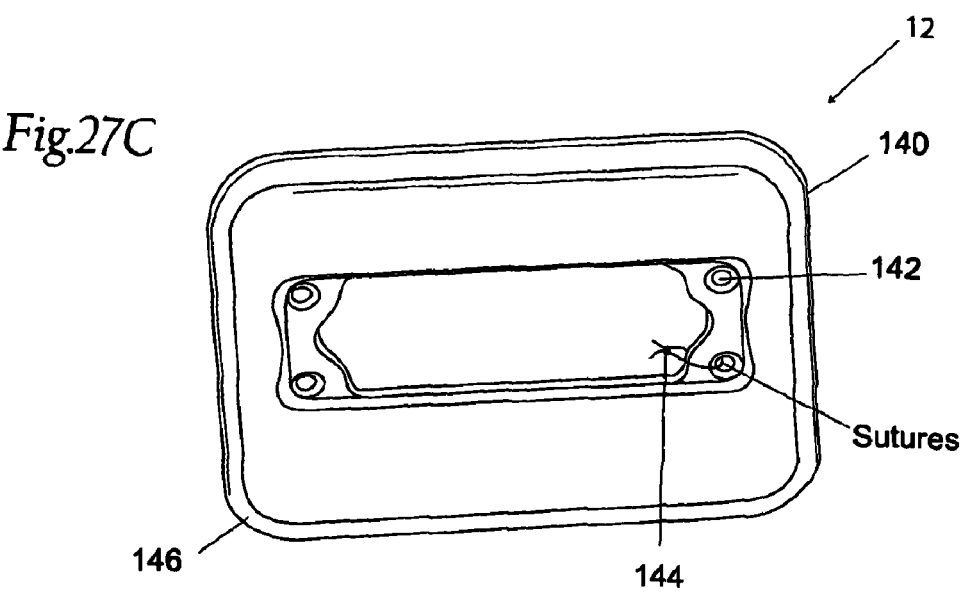

Another way to limit stress on a given implant 140 is to include apertures 142 through which external fixation means, such as sutures 144 or staples can be passed to attach the implant to surrounding tissue, as illustrated in FIG. 27C. This attachment may be to either superior or inferior tissue. This design will limit the amount of force applied at the implant edges and prevent motions that can lead to migration of the implant or extrusion. Rounded corners 146 are also provided to allow for less trauma to be applied to the surrounding tissues.

An alternative way to stabilize implants is by providing for in-tissue growth as net arrays do. For example, FIG. 27D is a plan view of a net array implant 150. Magnets 152 are linked together by a net-like webbing with flanges 154 surrounding each of the magnets or ferrous shapes. Each magnetic disk 152 is linked to the adjacent magnetic disk by a cross web 156, providing protection and isolation from body fluids and tissue. Openings 158 provide large areas in which the opposing surfaces of the surgically produced pocket may be closed for fast rejoining and healing of surfaces.

FIG. 27E shows an alternative embodiment of a net array implant 160 comprising magnets 162. In this embodiment the flanges 164 are linked together around the outside of the array. Also cross-ties 166 diagonally join the disks 156, to provide further stabilization. Openings 168 allow for tissue in-growth.

The magnetic net arrays 150 and 160 provide highly stable implanted magnetic devices, overcoming the difficulties related to migration magnet, flipping and inadequate forces needed to prevent occlusion of the airway during a sleep-related obstructive breathing event.

FIG. 27F shows an alternate embodiment of a magnetic implant 170 having a profile that is also designed to discourage migration. The implant's flowing curves permit a large area of the surrounding tissues to grow around and grip the implant thus providing a natural anchor. This implant 170 is particularly well suited for implantation in the tongue, which has a naturally curved morphology that matches to profile of the implant 170. The rounded corners 172 and the beveled edges 174 further allow for less trauma to be applied to the surrounding tissues. The middle of the implant allows a large space for tissue in-growth 178.

Figure 27G:
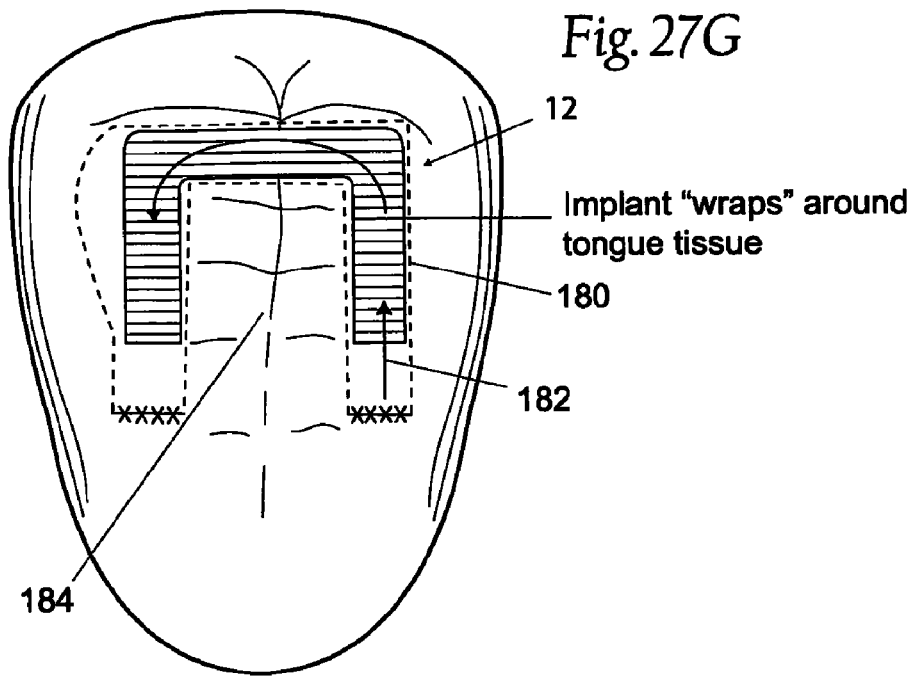
Figure 27H:
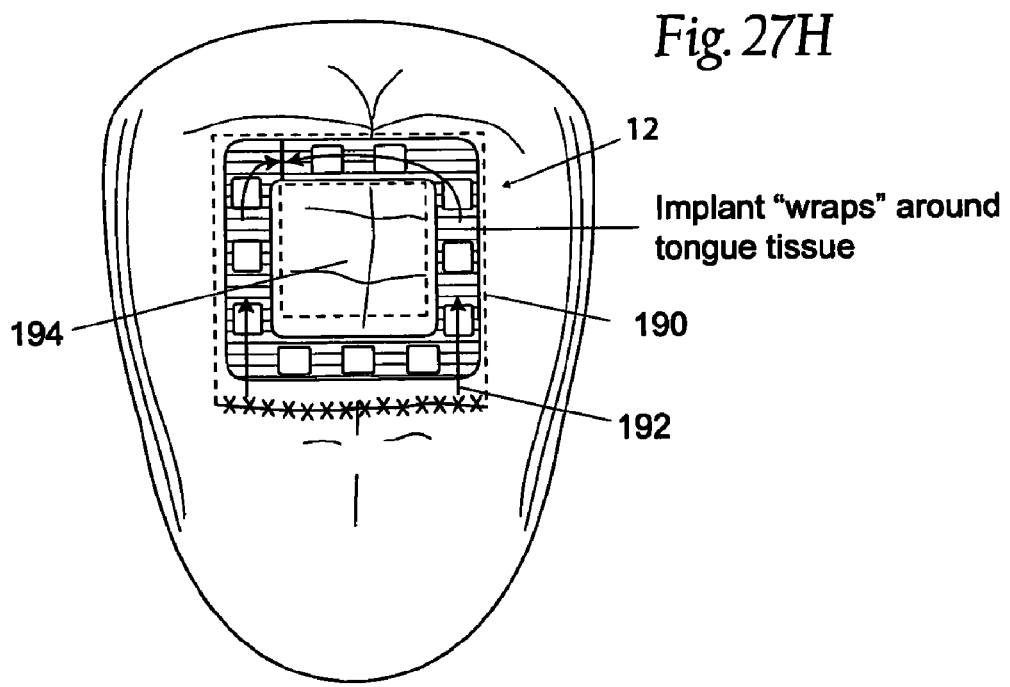

Alternatively, the tongue implant may wrap itself around tongue tissue (see FIGS. 27G/H) in such a fashion so as to prevent migration. FIG. 27G shows a U-shaped implant 180 placed in a tissue pocket 182 of the same shape (e.g., in the tongue). The tissue 184 in the center of the implant 180 is left substantially intact. The implant's shape is keyed to prevent migration, insure precise position by defining a specific implant pocket location, and limit relative tissue-to-implant motion. FIG. 27H shows an O-shaped implant 190 placed in a tissue pocket 192 of the same shape (e.g. in a tongue). As with the U-shaped implant 180, the O-shaped implant 190 leaves tissue 194 in the center of the implant 190 substantially intact. This implant shape is also keyed to prevent migration, insure precise position by defining a specific implant pocket location, and limit relative tissue-to-implant motion.

IV. Magnetic Structures for the Pharyngeal Wall

As previously described, the different embodiments of the magnetic force system 10 have included a magnetic structure or magnetic component 14 sized and configured to be placed on or in the pharyngeal wall in repelling magnetic alignment with the magnetic structure or magnetic component 12 in the tongue.

FIGS. 28A/B show a representative embodiment of a magnetic structure or magnetic component 14 sized and configured for implantation in a pharyngeal wall in association with a magnetic structure or magnetic component 12 implanted in a tongue, or another tissue mass facing the pharyngeal wall across the airway, e.g., the soft palate. The magnetic structure or magnetic component 14 comprises a support structure 200 that carries an array of magnetic components 18.

As before described, the support structure 200 can comprise a flexible or compliant material, for example, a woven, formed, or molded structure made, e.g., from a polymer or fiber or fabric or non-ferrous metallic material. The support structure 200 can be variously shaped, sized, and configured for implantation in the pharyngeal wall. The support structure 200 desirably includes features to impart stability and comfort while implanted. For example, the support structure 200 can include integrated fixation tabs 208 that extend outward from the main body of the structure 200 to engage adjacent tissue and provide enhanced fixation and stabilization. The structure 200 also desirably includes holes 210 for tissue in-growth or the placement of a tissue in-growth promoting material or bio-adhesive.

In FIGS. 28A/B, the magnetic components 18 comprise three permanent magnets 202, 204, and 206, arranged in a side-by-side relationship on the support structure 200. In this arrangement, the magnet 204 is placed in a middle region of the structure 200, and the magnets 202 and 204 are placed in opposite side regions of the structure 200. In use, as FIG. 29 shows, the structure 200 is intended to be implanted along the midline of the posterior pharyngeal wall, across from the selected soft palate magnetic structure or magnetic component 12. As before described, the facing implant can be implanted in a tongue instead of a soft palate, depending upon type of the apneic event being treated.

As shown in FIGS. 28A/B, the magnetic field of the N-pole of the middle magnet 204 is directed normal to the plane of the support structure 200. When implanted, the magnetic field of the N-pole is oriented in the direction of the airway. Accordingly, the magnetic field of the N-pole of the facing magnetic structure or magnetic component 12 (see FIG. 29) is generally aligned with the N-pole of the center magnet 204, to create the intended repelling magnetic field effect, which resists collapse of the tongue against the pharyngeal wall, as previously described.

As FIGS. 28A/B show, the directions of the magnetic fields of the N-poles of the end region magnets 202 and 206 are oriented at an angle B relative to the direction of the magnetic field of the N-Pole of the center magnet 204. As shown in FIGS. 28A/B, the angle B is between 0-degrees and 90-degrees. Stated differently (as FIG. 28B best shows), designating the direction of the magnetic field of the N-pole of the center magnet 204 as the z-axis, and designating the end regions as being spaced with the center magnet 204 along the x-axis, the magnetic fields of the N-poles of the end region magnets 202 and 206 project an angle B in opposite directions along the x-axis.

Figure 30:
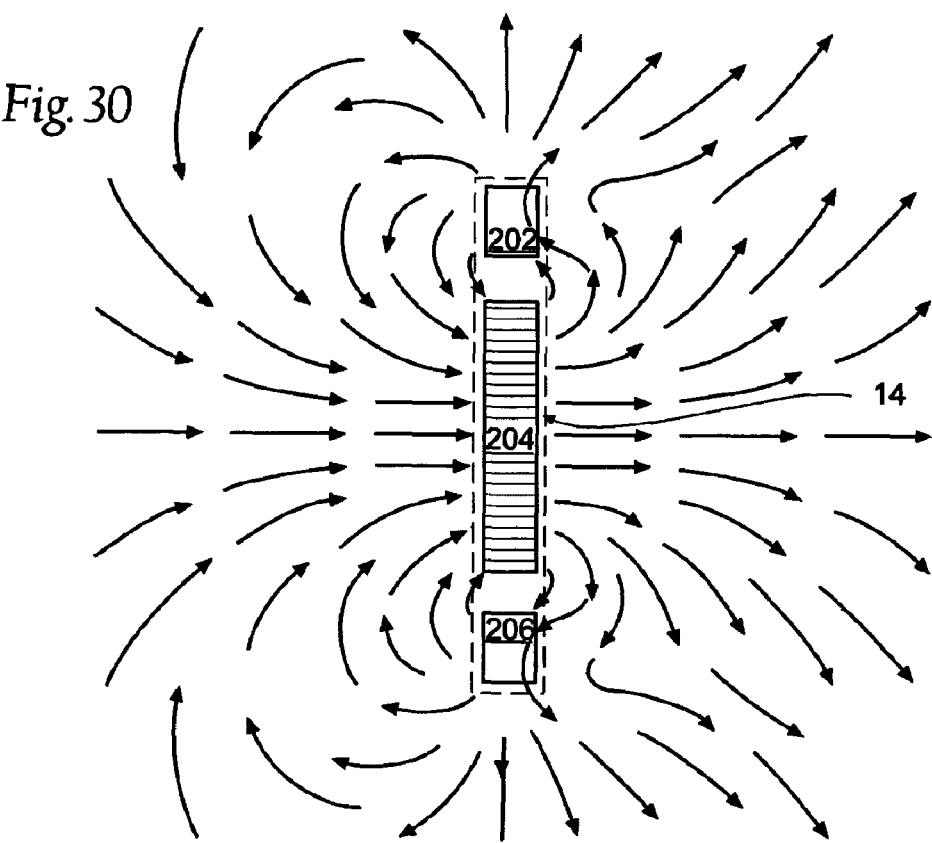
FIG. 30 is diagrammatically based upon finite element analysis the flux distribution of the z-axis field component of the pharyngeal wall implant, where the laterally-placed magnets have angled fields.
Figure 31:
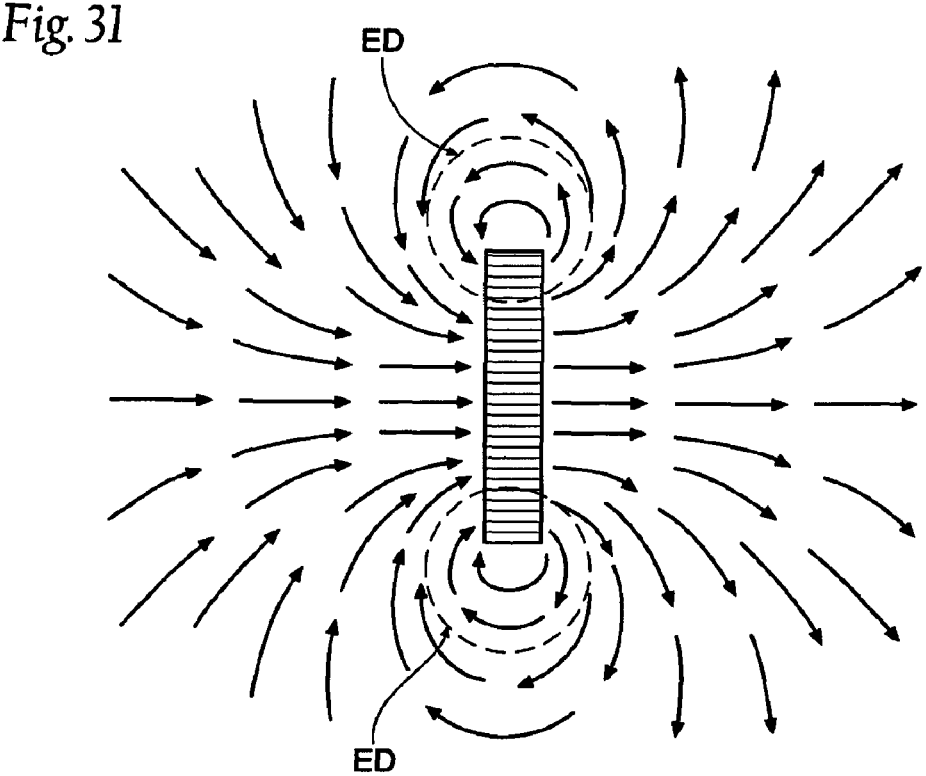
FIG. 31 is diagrammatically based upon finite element analysis the flux distribution of the z-axis field component of the pharyngeal wall implant, where all the magnets have the same field direction, parallel to the z-axis.

FIG. 30 shows, somewhat diagrammatically based upon finite element analysis, the flux distribution of the z-axis field component of the magnetic structure or magnetic component 14 shown in FIGS. 28A and 29, in which the directions of the magnetic fields of the N-poles of the end region magnets 202 and 206 are oriented at an angle B relative to the direction of the magnetic field of the N-Pole of the center magnet 204. It is the z-axis field component that projects across the airway and magnetically interacts (by repelling) with the facing soft palate (or tongue) implant. FIG. 31 shows, in comparison, the flux distribution of the z-axis field component of an implant like that shown in FIGS. 28A and 29, but in which the direction of the N-pole magnetic field of all magnets 202, 204, and 206 are parallel along the z-axis. By comparing FIGS. 30 and 31, it can be seen that the flux distribution of the magnetic array shown in FIGS. 28A and 29 more uniformly projects the repelling z-axis field component across the airway, without the edge discontinuities indicated by ED in FIG. 31. It is these edge discontinuities that can lead to misalignment of the repelling magnetic fields and to undesirable torque and decentering effects, as described above.

Figure 32:
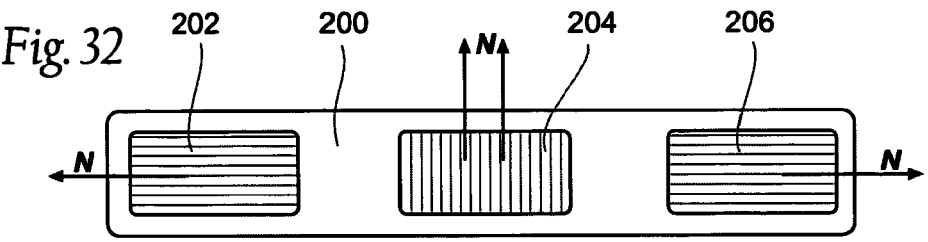
FIG. 32 shows a longitudinal cross-section of a magnetic pharyngeal wall implant with angled magnetic fields.

An implant having a more uniform magnetic flux distribution as shown in FIG. 30 can be manufactured in various ways. For example, as shown in FIG. 32, permanent magnets 202, 204, and 206 can be physically mounted and affixed, after magnetization, on a carrier support structure 200.

Figure 33A:
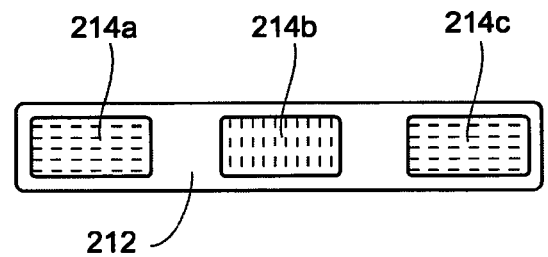
FIGS. 33A/B/C and 34A/B/C show pharyngeal wall implants with angled magnetic fields and the alternative processes for magnetizing pharyngeal wall implants so as to produce angled magnetic fields.
Figure 33B:
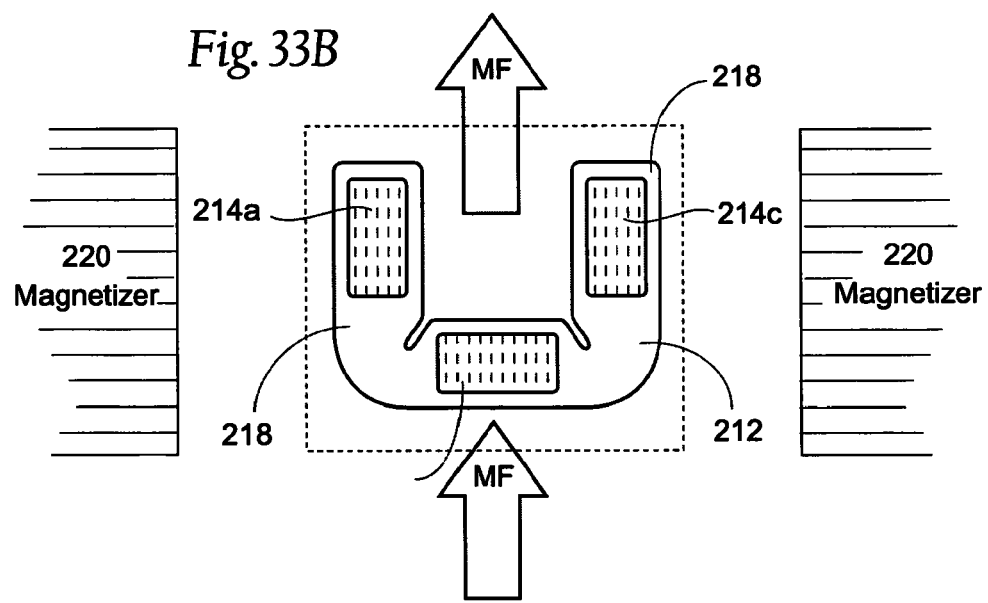
Figure 33C:
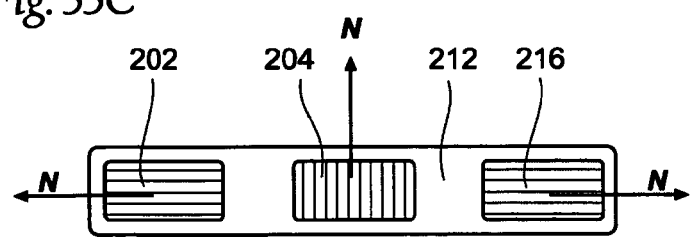

Alternatively, as FIGS. 33A, 33B, and 33C show, material 214a, 214b, and 214c that can be permanently magnetized (e.g., an alloy of Neodymium-Iron-Boron) and placed on a foldable carrier support 212, prior to undergoing magnetization, while the carrier support 212 is in a flat condition (see FIG. 33A). The grain directions of the material 214a, 214b, and 214c (indicated by dashed lines in FIG. 33A) are oriented and fixed prior to magnetization on the support carrier 212 to align with the intended direction of N-pole magnetic field following magnetization (i.e., the material 214b, after magnetization, is to become the center magnet 204, and the materials 214a and 214c are, after magnetization, to become the edge region magnets, respectively 202 and 206). The carrier support 212 is folded along two fold lines (see FIG. 33B), with the material 214b occupying the middle 216 of the folded structure, and the materials 214a and 214c on up-folded wings 218 of the structure. The structure 212 is placed in a conventional magnetizer 220 in this folded orientation (FIG. 33B), and the field of the magnetizer applied (as shown by the arrow MF in FIG. 33B) to magnetize the materials 214a, 214b, and 214c along their grains. Removed from the magnetizer 220 and unfolded (FIG. 33C), the result provides on the support carrier 212 permanent magnets 202, 204, and 206 having magnetic force fields that provide the uniform magnetic flux distribution as shown in FIG. 30.

Figure 34A:
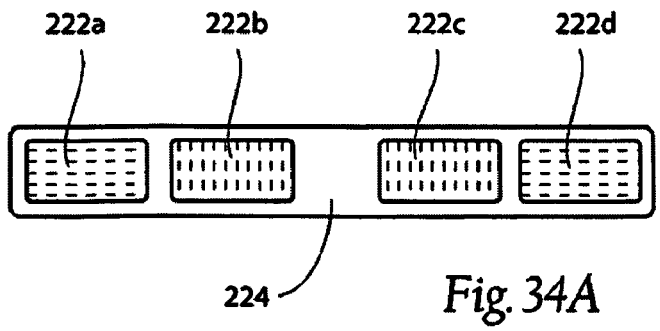
Figure 34B:
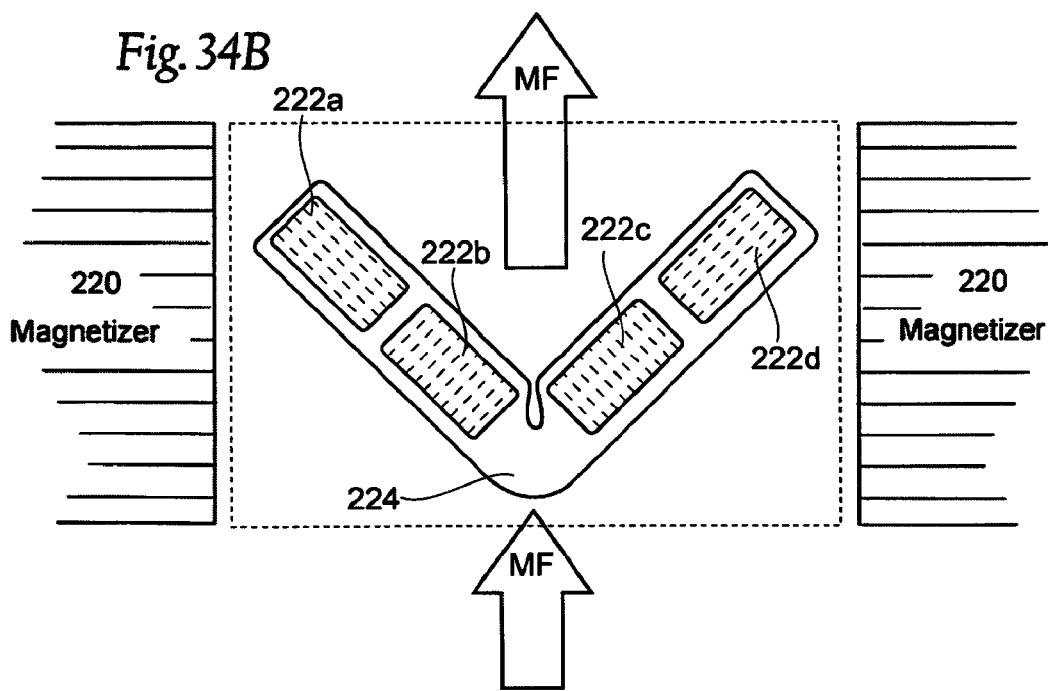
Figure 34C:
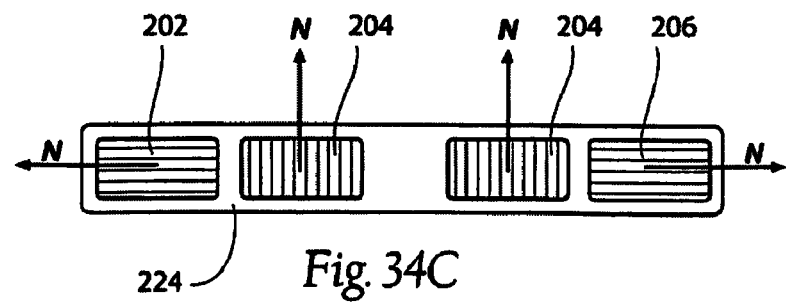

As shown in FIGS. 34A, 34B, and 34C, material 222a, 222b, 222c, and 222d can be permanently magnetized (e.g., an alloy of Neodymium-Iron-Boron) and be placed on a foldable carrier support 224, prior to undergoing magnetization, while the carrier support 224 is in a flat condition (see FIG. 34A). The grain directions of the material 222a, 222b, 222c, and 222d (indicated by dashed lines in FIG. 34A) are oriented and fixed prior to magnetization on the support carrier 224 to align with the intended direction of N-pole magnetic field following magnetization (i.e., the materials 222b and 222c, after magnetization, are to become the center magnets 204, and the materials 222a and 222d are, after magnetization, to become the edge region magnets, respectively 202 and 206). The carrier support 224 is folded along one fold line in half (see FIG. 34B), with the materials 222a and 222b occupying one side of the fold line and the materials 222c and 222d occupying the other side of the fold line. The structure 224 is placed in a conventional magnetizer 220 in this folded condition (FIG. 34B), and the fold oriented to assure that the grain direction is within 45-degrees and 60-degrees of the magnetizing field (as shown by the arrow MF in FIG. 34B). The field MF magnetizes the materials 222a, 222b, 222C, and 222d along their grains. It has been determined that the desired orientation of magnetic fields can be achieved provided that the grain direction, when folded within the magnetizer, is within 45-degrees and 60-degrees of the field of magnetization. Removed from the magnetizer 220 and unfolded (FIG. 34C), the result provides on the support carrier 224 permanent magnets 202, 204, and 206 having magnetic force fields that provide the uniform magnetic flux distribution as shown in FIG. 30.

Alternatively, as FIGS. 35A and 35B show, a three piece support carrier 226 comprising components 226a, 226b, and 226c can be provided (see FIG. 35A). The component 226b carries the middle permanent magnet 204. The components 226a and 226c carry the end region magnets 202 and 206, respectively. The components 226a, 226b, and 226c are manufactured and magnetized as separate units, as FIG. 35A shows. At time of implantation, the components 226a, 226b, and 226c are assembled in situ (see FIG. 35B), to form a composite implant with the permanent magnets 202, 204, and 206 with magnetic fields that are oriented to provide the uniform magnetic flux distribution as shown in FIG. 30.

FIGS. 36A and 36B show an alternative embodiment of a three piece support carrier 228. In FIGS. 35A and 35B, the end region components 228a and 228c each couple to the middle component 226b by snap-fit that interlocks to the middle component 228b by a single end-on locking tab 230.

The size and configuration of the permanent magnets 202, 204, and 206 can differ. Each or any permanent magnet 202 or 204 or 206 can comprise a structure formed by single magnet (as FIGS. 33A/B/C and 36A/B show), or each or any permanent magnet 202 or 204 or 206 can comprise a structure formed by multiple magnets magnetized in the same direction (as FIGS. 34A/B/C and FIGS. 35A/B show). Furthermore, each or any permanent magnet 202 or 204 or 206 can comprise a radial or variable magnetic field magnet(s).

V. Magnetic Structures for the External Source of Magnetic Force

Figure 37:
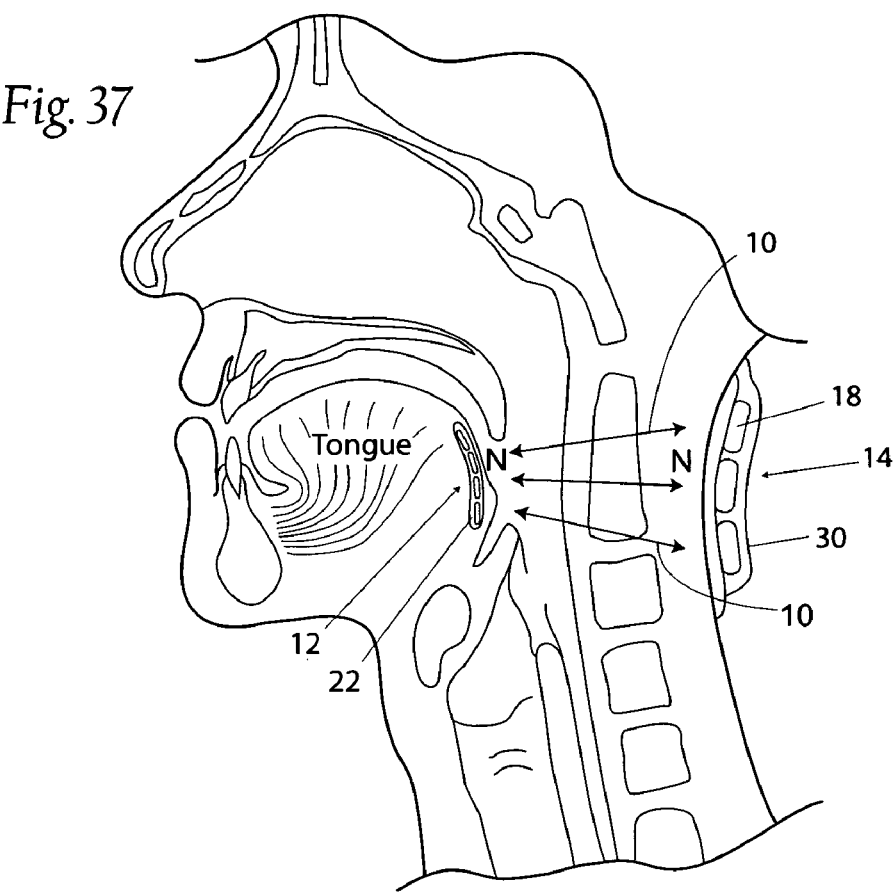
FIGS. 37/38 show a sagittal view and a horizontal cross-sectional view of a human upper respiratory system utilizing an illustrative repelling magnetic force system using a magnetic tongue implant and an external repelling magnet system.

FIG. 37 shows a magnetic repelling collar. Magnets 18 are mounted in a form fitting collar such that the magnet is positioned against the back of the neck at the level of the tongue. The magnet or magnets 18 will all be oriented such that the anterior facing surface of the magnet(s) will be north or south, depending on the orientation of the implanted magnetic elements in the array. The intent is to orient both the implanted magnets and the collar borne magnets to provide a repelling action between the two sets of magnets.

In the case of both the implanted magnets and those in the collar, there may be multiple magnets or simply single magnets providing that sufficient repelling force is available to prevent the occlusion of the airway during sleep. It will be recognized that for stability and to keep the size of the implanted magnets as small as possible, the multiple magnet scheme in the implanted array will be the preferred embodiment. In the larger collar borne magnets, single or multiple magnets may be employed within the intent of this invention.

Figure 38:
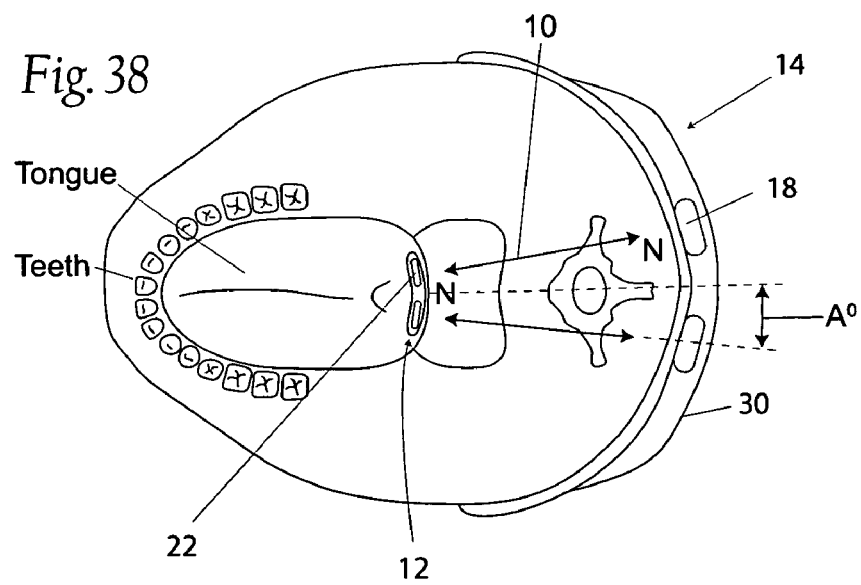

FIG. 38 shows a horizontal cross-section of a human oral cavity, cut just above the upper surface of the tongue. The implanted magnetic array 22 opposes the collar magnets 18, resulting in repelling forces between the implanted magnets and collar magnets. Two columns of magnets 18 are arranged angularly 240 on each side of the centerline of the neck. The angle of lateral arrangement of the collar magnets may be varied to provide stability in the tongue while the collar is being worn. It can be seen that use of a single magnet or single column of magnets in the collar may result in causing the tongue to move laterally, away from the repelling collar magnets. With two columns of magnets (or 2 single laterally arranged magnets) a triangular balance between the repelling forces arises which provides stability.

Figure 39:
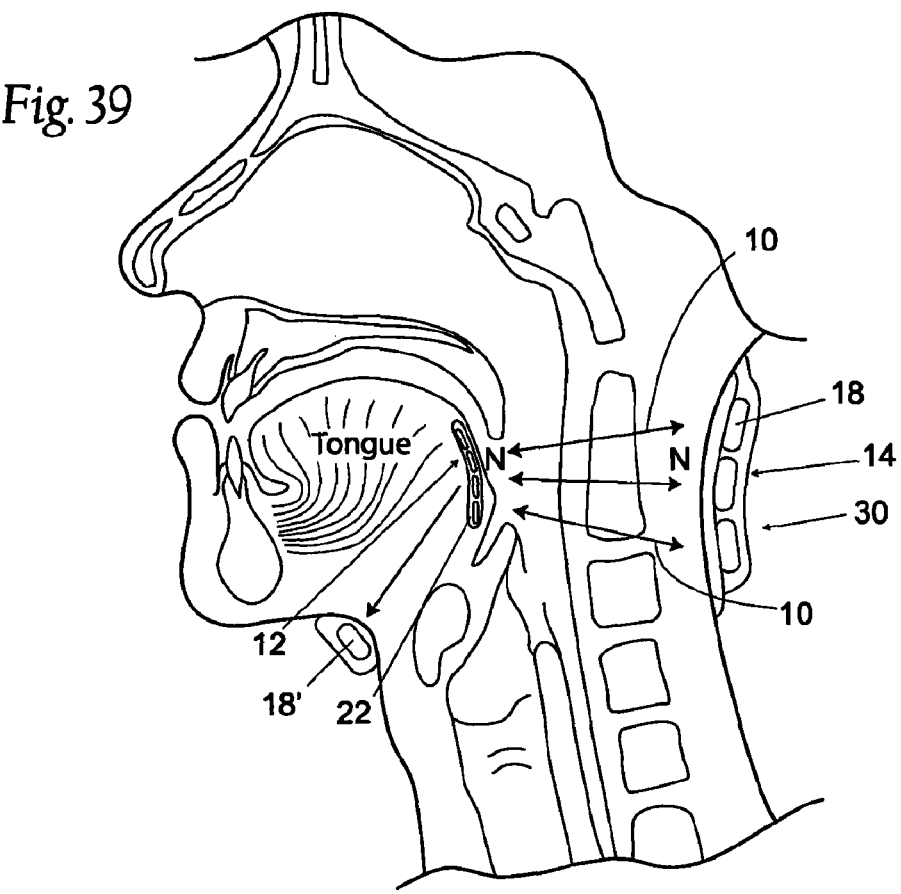
FIGS. 39/40 show a sagittal and cross-sectional view of a human upper respiratory system utilizing an illustrative a magnetic force system that is both repelling and attracting using a magnetic tongue implant and an external magnet system.
Figure 40:
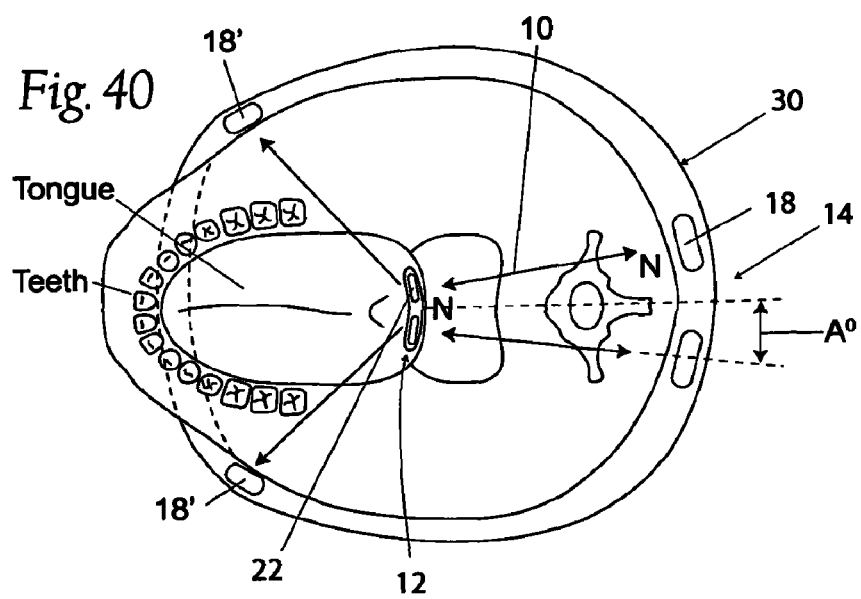

FIGS. 39/40 show an alternative external source of magnetic force. Magnets 18' are mounted in a form fitting collar such that the magnet is positioned against the back of the neck at the level of the tongue. In the anterior part of the collar that fits under the jaw, the magnet or magnets 18' will be oriented so that they will magnetically interact and attract the implanted magnets. In the posterior part of the collar that fits around the back of the neck, the magnet or magnets 18 will all be oriented such that the implanted magnets and the collar borne magnets to provide a repelling action between the two sets of magnets. The combination of attracting and repelling magnetic forces on the magnetic tongue implant will aid in stabilizing the position of the tongue even further than other magnetic systems.

In the case of both the implanted magnets and those in the collar, there may be multiple magnets or simply single magnets providing that sufficient repelling force is available to prevent the occlusion of the airway during sleep. It will be recognized that for stability and to keep the size of the implanted magnets as small as possible, the multiple magnet scheme in the implanted array will be the preferred embodiment. In the larger collar borne magnets, single or multiple magnets may be employed within the intent of this invention.

External repelling magnet systems provide advantages from both decreased tissue trauma and ability to control the magnetic force. With regard to tissue trauma, as the tongue is moved further away from the strong collar magnets, the amount of force applied to the implanted magnets will be reduced. This will result in fewer problems with movement of the implant in tissue caused by magnetic force. The incision bearing the implanted device can be allowed to heal fully before the magnetic forces are applied. Rejoining of tissue and attachment to the implant can be allowed to develop completely without disturbing forces.

With regard to the ability to control the magnetic force, the amount of force can readily be titrated or adjusted. Very large forces can be exerted by use of large external magnets. Electromagnets may be employed in place of permanent or rare earth magnets, allowing adjustment of forces during sleep as managed by electronic sensing means. In other words, force might be applied only as needed or called for by apneic events.

VI. Storage Carrying Case

Figure 41:
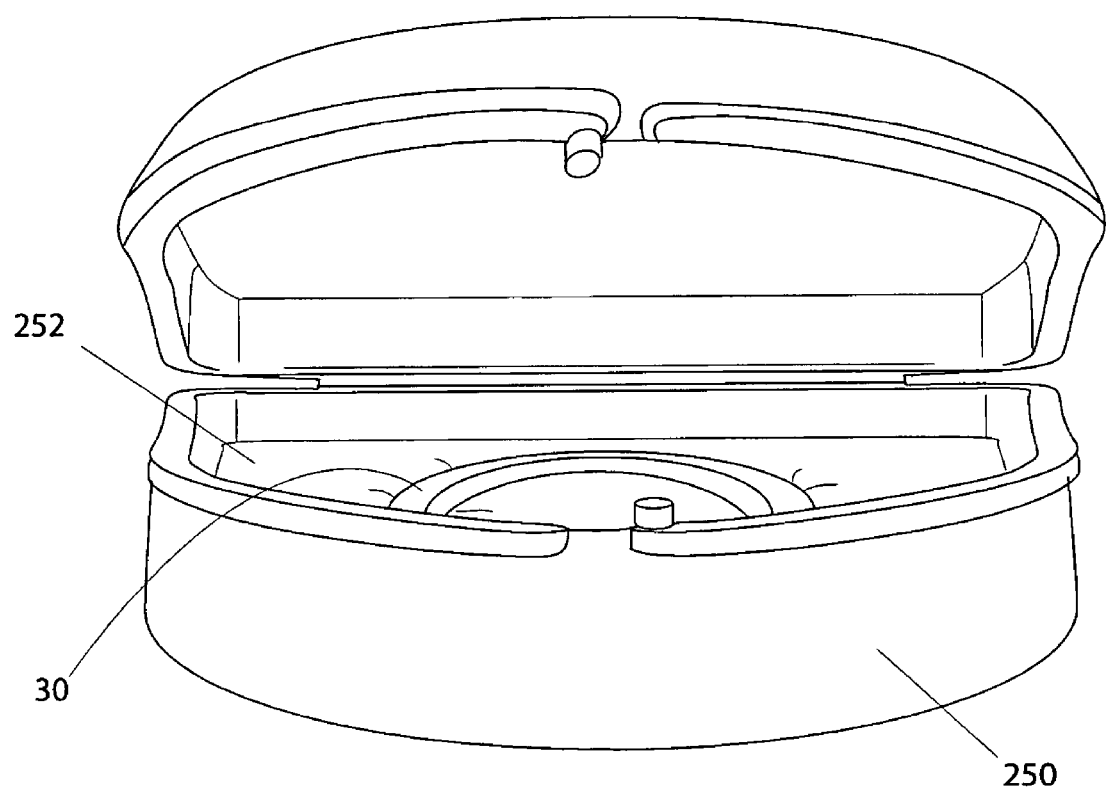
FIG. 41 shows an illustrative storage case for external magnetic components.

FIG. 41 shows a storage carrying case 250 for external magnetic components. The removable magnetic device 30 should be placed in a magnetically shielded carrying case 250. The magnet keeper has north and south poles. The magnetic device is either partially or completely surrounded in a metal or composite metal box. The inside of the protective storage carrying case is padded with a mixture of silicone and metal particles that shield the magnetic forces 252, as well as protect the magnet from potential breakage or chipping.

VI. Force Required to Maintain a Patent Airway

Figure 42:
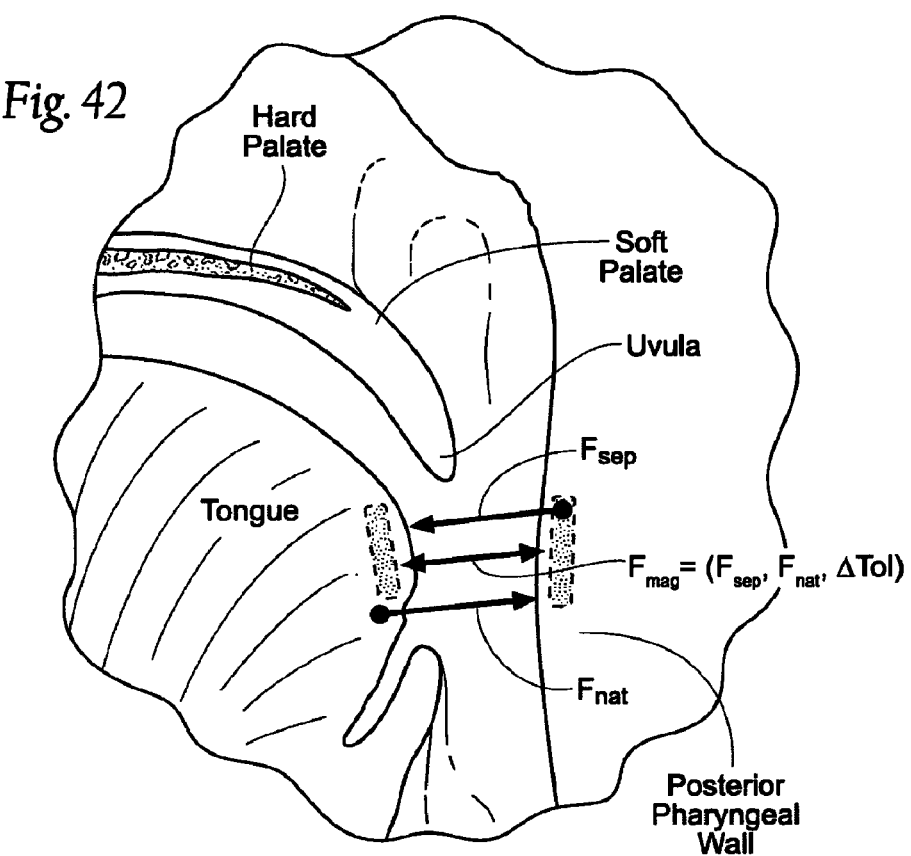
FIG. 42 is an anatomic sagittal view of the tongue and pharyngeal wall, showing the resolution of forces F-sep and F-nat to provide an optimal therapeutic force F-mag that, at night, resists collapse of the tongue against the pharyngeal wall during sleep, yet does not affect speech, swallowing or drinking during normal activities awake or asleep.

As just described, and as FIG. 42 shows in a diagrammatic way, for a given individual, a magnitude can be assigned to a force required to separate tongue tissue from the posterior pharyngeal wall, to thereby resist the collapse of an airway during an apneic episode. This force, designated F-sep in FIG. 42, can be obtained by physical measurement of a given individual, or it can based upon measurements taken during a cadaver study, or it can be selected empirically based upon general anatomic considerations for a population of individuals, or a combination of these and other considerations.

For a given individual, a magnitude can also be assigned a counterbalancing force (designated F-nat in FIG. 33), which represents the force exerted by natural muscular activity upon the tongue, to enable swallowing, chewing, or speech during normal airway function. The force F-nat can be also obtained by physical measurement of a given individual, or it can be selected empirically based upon general anatomic considerations for a population of individuals, or a combination of these and other considerations.

As shown in FIG. 42, the magnetic force (F-mag) that a system 10 develops can be expressed as a function of F-sep and F-nat, or F-mag=f(F-sep, F-nat). The magnetic force can comprise a repelling force (i.e., a force in essentially an anterior-posterior direction between the tongue and posterior pharyngeal wall), and/or a torquing force (i.e., a force or moment of a force that tends to rotate the tongue about an axis), and/or decentering force (i.e., a force in essentially a lateral or side-to-side direction that tends to offset the tongue left or right), or a combination of two or more of these forces. The magnetic force F-mag maintains separation between the tongue and the posterior pharyngeal wall, which is the desired therapeutic effect.

The function desirably incorporates the premise that F-sep≦F-nat., such that F-nat can overcome F-sep to preserve normal airway function. In effect, F-nat is the upper limit for the amount of force used which, to achieve an effective OSA therapy, which F-sep should not exceed. The function also desirably incorporates the premise that F-mag≧F-sep, so that the desired separation between the tongue and the posterior pharyngeal wall is maintained.

The function resolves F-sep and F-nat to provide an optimal therapeutic force that, at night, resists collapse of the tongue against the pharyngeal wall during sleep, yet does not affect speech, swallowing or drinking during normal activities awake or asleep. Since it is only used at night, CPAP can be removed, thus eliminating any effect on speech or swallowing during daytime hours or non-treatment. An implanted tongue and pharyngeal wall system is "turned on" all the time as the magnets cannot be easily removed and therefore must deal with the issue of preserving normal airway function while treating OSA or snoring.

The function also desirably includes a tolerance factor ΔTol, which takes into account that F-nat can increase with time after implantation, as an individual develops tolerance to F-mag. F-nat can thereby increase with time after implantation, as the individual trains his or herself to exert more force during swallowing or speech in the presence of F-mag to maintain normal airway function. The nature of the tolerance factor ΔTol can be ascertained by physical measurement of a given individual, or it can be selected empirically based upon general anatomic considerations for a population of individuals, or a combination of these and other considerations.

Further, in arriving at the absolute magnitude of F-sep, it has been discovered that the moderation of non-uniform edge discontinuities, previously described and shown in FIGS. 30 and 31, is an import design criteria, particular for the implant placed in the posterior pharyngeal wall. Due to these edge discontinuities, it has been discovered that F-sep has two components. The first component is the desired therapeutic force F(z) that is developed in an anterior-to-posterior direction, which prevents the tongue from falling back upon the posterior pharyngeal wall. The second component is an undesired decentralizing side loading force F(y) that is exerted due to the edge discontinuities, which moves the tongue laterally, i.e., to the side. A desired therapeutic force magnitude F(z) can, if the edge discontinuities are not moderated, undesirably move the tongue laterally. The magnitude of the edge discontinuities, i.e., the magnitude of F(y), can be titrated and controlled by the design of the pharyngeal wall implant in the manners previously described, e.g., by directing the magnetic fields of end region magnet(s) at an angle B relative to the direction of the center region magnet(s), as shown in FIGS. 28A/B. Further, by stabilization of the tongue implant in the manners previously described, e.g., as shown in FIGS. 27A to 27 H, the destabilizing effects of F(y) can be also counteracted.

Figure 43:
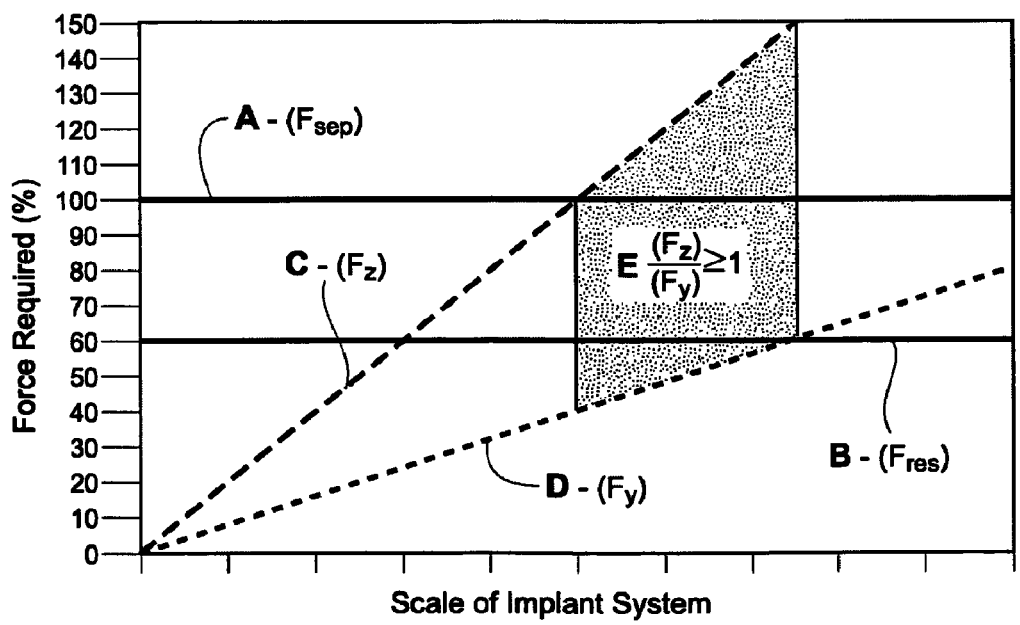
FIG. 43 is a chart executing an implant force scaling strategy.

An implant force scaling strategy like that shown in FIG. 43 can be based upon an appreciation of these considerations. In FIG. 43, the magnitude of a force applied in an anterior-posterior direction upon the tongue necessary to achieve the desired therapeutic effect (i.e., F-sep) is indicated at A. As before indicated, this is the force required to separate tongue tissue from the posterior pharyngeal wall, to thereby resist the collapse of an airway during an apneic episode. The force F-sep (also shown in FIG. 42), can be obtained by physical measurement or selected empirically based upon general anatomic considerations for a population of individuals, or a combination of these and other considerations.

In FIG. 43, the magnitude of the resistance (F-res) of a given tongue decentered medially in response to an external side load is indicated at B. The specific magnitude of F-res can be obtained by physical measurement of a given individual, or it can be based upon cadaver studies, or it can be selected empirically based upon general anatomic considerations for a population of individuals, or a combination of these and other considerations. In FIG. 43, the magnitude of F-res (B) is expressed as a percentage of F-sep (A). That is, on the y-axis, F-sep (A) is expressed as 100% and F-res (B) is expressed as 60%. The particular relationship between F-sep and F-res can vary based upon anatomic considerations.

In FIG. 43, the magnitude of the anterior-to-posterior force F(z) generated by a given pharyngeal wall implant is indicated by C. As FIG. 43 shows by the slope of C, this magnitude of F(z) will vary as a function of distance between the pharyngeal wall implant and the tongue implant, as well as a function of the particular structural characteristics and stabilization of the tongue implant itself.

In FIG. 43, the magnitude of the side load force F(y) generated by the given pharyngeal wall implant is indicated by D. The slope and magnitude of D will vary based upon the design of the pharyngeal wall implant, particularly with respect to the moderation of edge discontinuities, as previously described. The slope and magnitude of D will also depend upon the particular structural characteristics and stabilization of the tongue implant itself.

For a given magnetic repelling force system affecting the tongue, the magnitude of F(z) with respect to the magnitude of F(y) represents an Implant Scaling Factor (F-scale). F-scale can be expressed as a ratio of F(z) to F(y); that is F-scale=F(z)/F(y). The magnitude of F-scale for a given magnetic repelling force system affecting the tongue indicates that the system is likely to achieve the desired therapeutic effect without decentering the tongue.

It has been discovered that, for a given magnetic repelling force system affecting the tongue, an F-scale≧1 is desirable. For a given magnetic repelling force system affecting the tongue, an F-scale<1 indicates that decentering of the tongue will occur, which offsets the desired therapeutic effect. An F-scale<1 indicates that the edge discontinuities of the pharyngeal wall implant should be reduced or moderated and/or means for stabilizing the tongue implant are warranted.

FIG. 43 also lends itself to an implant force scaling strategy. The intersections of C and D with A and B define an optimal operating region E for a magnetic repelling force system affecting the tongue. In region E, F(z) is at or above the magnitude that achieves the desired therapeutic effect but where F(y) is not at the magnitude at which side loading (i.e., decentering of the tongue) will occur.

Experimentally, it has been determined that the force likely required to keep an airway open on a cadaver using a magnetic force system that operates by repulsion is no more than 200 g. It is believed that magnetic tongue implant systems require a force of about 2 to about 150 g to maintain a patent airway. More specifically, a force in the range of about 5 to about 100 g is believed to provide the desired therapeutic benefits in combination with control of edge discontinuities in the pharyngeal wall implant and stabilization of the tongue implant.

VII. Conclusion

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

The above-described embodiments of this invention are merely descriptive of its principles and are not to be limited. The scope of this invention instead shall be determined from the scope of the following claims, including their equivalents.

We claim:

1. A magnetic system comprising:
a first magnetic structure sized and configured for placement in or on a tongue; and
a second magnetic structure sized and configure for placement in or on a pharyngeal wall,
wherein at least one of the first and second magnetic structures include magnetic materials that are sized, configured, and arranged thereon to maintain a substantially mutually repelling orientation between the first and second magnetic structures during a native range of movement of the tongue relative to the pharyngeal wall during at least one of swallowing, drinking or speech, wherein each of the magnetic materials includes a top surface and an opposite bottom surface, and wherein the top surfaces of each of the magnetic materials are disposed in an arrangement having a curved shape.

2. A system according to claim 1 wherein at least one of the first and second magnetic structures is capable of flexure in response to application of an external force.

3. A system according to claim 1 wherein at least one of the first and second magnetic structures is capable of flexure in response to application of an external force more in one direction than in another direction.

4. A method comprising:
providing a magnetic system comprising:
a first magnetic structure sized and configured for placement in or on a tongue,
a second magnetic structure sized and configure for placement in or on a pharyngeal wall, wherein at least one of the first and second magnetic structures include magnetic materials that are sized, configured, and arranged thereon to maintain a substantially mutually repelling orientation between the first and second magnetic structures during a native range of movement of the tongue relative to the pharyngeal wall during swallowing and/or drinking/and or speech; and
placing the first magnetic structure in or on a tongue and placing the second magnetic structure in or on a pharyngeal wall.

5. A magnetic structure comprising:
a carrier sized and configured for placement in or on tissue, the carrier defining a top surface and a bottom surface, the top and bottom surfaces having curved configurations disposed generally parallel to each other, and
a magnetic material carried by the carrier,
wherein the magnetic material is generally disposed in a curvilinear plane between the top and bottom surfaces.

6. A magnetic structure according to claim 5 wherein the curved configuration includes a first curved configuration along a first axis of the magnetic structure and a second curved configuration along a second axis of the magnetic structure.

7. A magnetic structure according to claim 5 wherein the magnetic material comprises first and second sources of magnetism, each source generating a magnetic field having a magnetic pole oriented in a direction, the direction of the magnetic pole of the first source of magnetism being oriented at a nonzero angle from the direction of the magnetic pole of the second source of magnetism.

8. A magnetic structure according to claim 5 wherein the magnetic material includes a radial magnet.

9. A magnetic structure according to claim 5 wherein the carrier is capable of flexure in response to application of an external force.

10. A magnetic structure according to claim 5 wherein the carrier is capable of flexure in response to application of an external force more in one direction than in another direction.

11. A system comprising
a first magnetic structure as defined in claim 5, and
a second magnetic structure sized and configured to be placed in or on tissue in a desired orientation with respect to the first magnetic structure to magnetically interact with the first magnetic structure.

12. A system according to claim 11 wherein the first magnetic structure is sized and configured to be placed in or on a tongue and wherein the second magnetic structure is sized and configured to be placed in or on tissue in a posterior pharyngeal wall.

13. A method comprising:
providing a system as defined in claim 12,
placing the first magnetic structure in or on tissue of a tongue, and
placing the second magnetic structure in or on a posterior pharyngeal wall.

14. A method comprising
providing a magnetic structure as defined in claim 5, and
placing the magnetic structure in or on tissue of a tongue.

* * * * *